(12) United States Patent
Kuang

(10) Patent No.: US 10,544,144 B2
(45) Date of Patent: Jan. 28, 2020

(54) FUSED PYRIMIDINE PIPERIDINE CYCLIC DERIVATIVE, PREPARATION PROCESS AND USE THEREOF

(71) Applicant: SHANGHAI ALLIST PHARMACEUTICAL AND MEDICAL TECHNOLOGY CORPORATIONS, Shanghai (CN)

(72) Inventor: Rongren Kuang, Shanghai (CN)

(73) Assignee: SHANGHAI ALLIST PHARMACEUTICAL AND MEDICAL TECHNOL, Shanghai (CN)

( * ) Notice: Subject to any disclaimer, the term of this patent is extended or adjusted under 35 U.S.C. 154(b) by 0 days.

(21) Appl. No.: 16/307,362

(22) PCT Filed: Jun. 1, 2017

(86) PCT No.: PCT/CN2017/086817
§ 371 (c)(1),
(2) Date: Dec. 5, 2018

(87) PCT Pub. No.: WO2017/211216
PCT Pub. Date: Dec. 14, 2017

(65) Prior Publication Data
US 2019/0218213 A1 Jul. 18, 2019

(30) Foreign Application Priority Data
Jun. 6, 2016 (CN) .......................... 2016 1 0392343

(51) Int. Cl.
C07D 471/04 (2006.01)
A61K 31/519 (2006.01)
A61P 35/00 (2006.01)
A61P 35/02 (2006.01)

(52) U.S. Cl.
CPC .......... *C07D 471/04* (2013.01); *A61K 31/519* (2013.01); *A61P 35/00* (2018.01); *A61P 35/02* (2018.01)

(58) Field of Classification Search
CPC .................................................. C07D 471/04
See application file for complete search history.

(56) References Cited

U.S. PATENT DOCUMENTS

| 8,440,679 B2 | 5/2013 | McAllister et al. |
| 8,552,002 B2 | 10/2013 | Ding et al. |
| 2013/0237538 A1 | 9/2013 | Hull, III et al. |

FOREIGN PATENT DOCUMENTS

| CN | 101035769 A | 9/2007 |
| CN | 101611014 A | 12/2009 |
| CN | 102858770 A | 1/2013 |
| EP | 1775298 A1 | 4/2007 |
| WO | WO-98/35985 A1 | 8/1998 |
| WO | WO-01/60814 A2 | 8/2001 |
| WO | WO-01/94341 A1 | 12/2001 |
| WO | WO-2006/000420 A1 | 1/2006 |
| WO | WO-2008/002816 A1 | 1/2008 |
| WO | WO-2008/075068 A2 | 6/2008 |
| WO | WO-2010/129509 A1 | 11/2010 |
| WO | WO-2011/027106 A1 | 3/2011 |
| WO | WO-2011/135376 A1 | 11/2011 |
| WO | WO-2014/007951 A2 | 1/2014 |

OTHER PUBLICATIONS

Jain et al. Breast Cancer Research, pp. 1-9. (Year: 2012).*
Cancer Drug Design and Discovery, Neidle, Stephen,ed. (Elsevier/Academic Press), pp. 427-431. (Year: 2008) (Year: 2008).*
International Search Report and Written Opinion for Application No. PCT/CN2017/086817, dated Jul. 27, 2017.
Kwabi-Addo et. al., "The role of fibroblast growth factors and their receptors in prostate cancer," Endocrine-Related Cancer, 11:709-724 (2004).

* cited by examiner

*Primary Examiner* — Emily A Bernhardt
(74) *Attorney, Agent, or Firm* — Marshall, Gerstein & Borun LLP

(57) ABSTRACT

The present invention relates to the fused pyrimidine piperidine cyclic derivative represented by the following formula (I) and a pharmaceutically acceptable salt thereof and a process for preparing the same, wherein R1, R2, R3, R4, R5, X, Y and Z are defined as in the description. The present invention further provides use of said fused pyrimidine piperidine cyclic derivative in manufacture of a medicament for preventing or treating FGFR kinase mediated disease such as cancer.

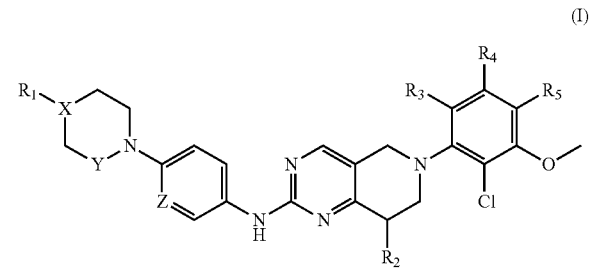

(I)

17 Claims, 1 Drawing Sheet

FUSED PYRIMIDINE PIPERIDINE CYCLIC DERIVATIVE, PREPARATION PROCESS AND USE THEREOF

TECHNICAL FIELD

The present invention relates to a fused pyrimidine piperidine cyclic derivative or a pharmaceutically acceptable salt thereof, a pharmaceutical composition containing said compound, a process for preparing said compound and use of said compound in treating or preventing FGFR kinase mediated disease such as cancer.

BACKGROUND

Fibroblast growth factor (FGF) has been recognized as an important mediator of many physiological processes, such as morphogenesis during development and angiogenesis. At present, there are more than 25 members known within FGF family. The fibroblast growth factor receptor (FGFR) family consists of four members (FGFR1, FGFR2, FGFR3 and FGFR4), which are glycoproteins composed of extracellular immunoglobulin (Ig)-like domains, a hydrophobic transmembrane region and a cytoplasmic part containing a tyrosine kinase domain. FGF binding leads to FGFR dimerization, followed by receptor autophosphorylation and activation of downstream signaling pathways. Receptor activation is sufficient for the recruitment and activation of specific downstream signaling partners that participate in the regulation of diverse processes such as cell growth, cell metabolism and cell survival. Thus, the FGF/FGFR signaling pathway has pleiotropic effects on many biological processes critical to tumor cell proliferation, migration, invasion, and angiogenesis.

There is now considerable evidence directly linking FGF signaling to human cancer. The elevated expression of various FGFs has been reported in a diverse range of tumor types such as bladder, renal cell and prostate. Activating mutations of various FGFRs have been associated with epidermal cancer, cervical cancer, bladder cancer and multiple myeloma whilst receptor expression has also been documented in prostate cancer, bladder cancer and the like (Grose, R. et. al., Cytokine & Growth Factor Reviews 2005, 16, p 179-186 and Kwabi-Addo, B. et. al., Endocrine-Related Cancer 2004, 11, p 709-724). For these reasons, the FGF signaling system is an highly potential therapeutic target, particularly since therapies targeting FGFRs and/or FGF signaling may affect both the tumor cells and tumor angiogenesis directly.

WO2006/000420A1 discloses a pyrimidine urea derivative having the following general formula as kinase inhibitor, and the representative compound is BGJ398 which is now in the clinical trial (phase II) in US for treating bladder cancer,

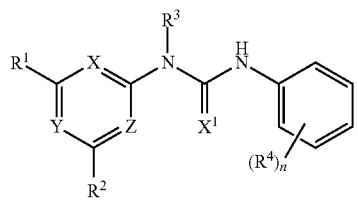

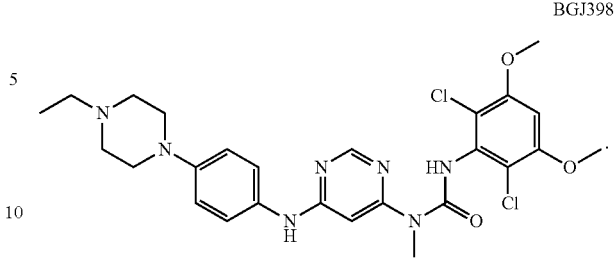

BGJ398

WO2008/075068A2 discloses an amidopyrazole-type compound having the following general formula as FGFR inhibitor, which includes the representative compound AZD4547, which is now in the clinical trial (phases II/III) in US for treating non-small cell lung cancer,

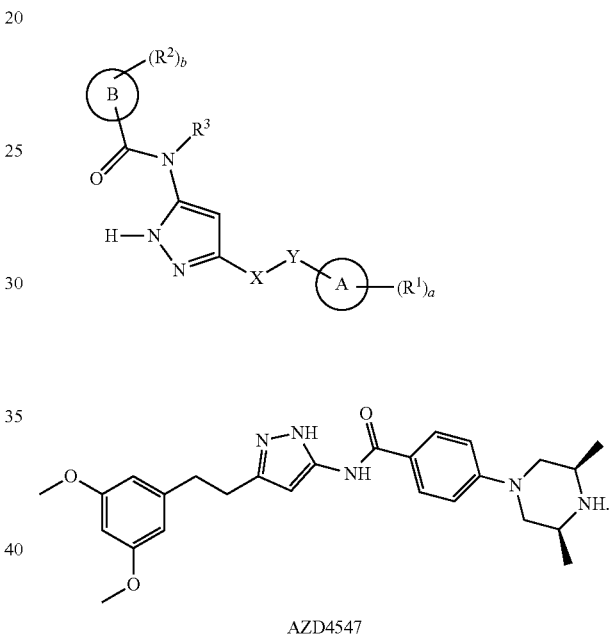

AZD4547

WO2010/129509A1 discloses a vinylindazole compound LY2874455 having the following general formula as a strong inhibitor for FGFR1 and FGFR3, which is now in the clinical trial (phase II) in US for treating cancer,

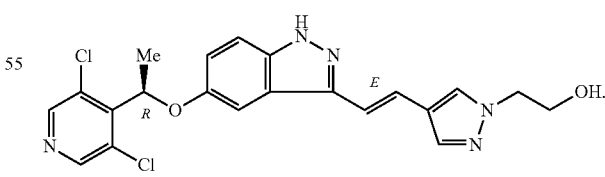

LY2874455

WO2011/135376A1 discloses a pyrazolylquinazoline kinase inhibitor having the following general formula as FGFR inhibitor, and the representative compound is JNJ42756493, which is now in the clinical trial (phase II) in US for treating urogenital system cancer,

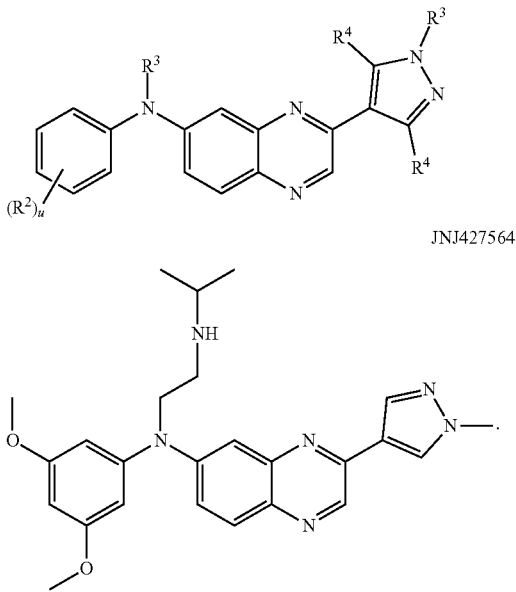

JNJ42756493

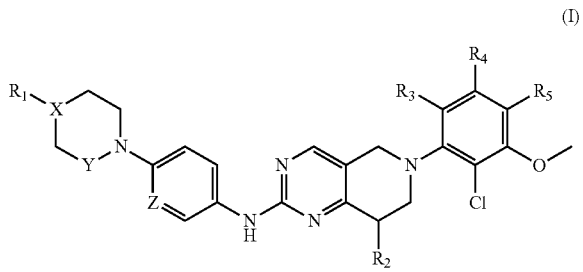

Currently, the domestic development for the FGFR inhibitors is in the preliminary stage. It is necessary for the clinical use to provide a new inhibitor that can inhibit the FGF signaling and effectively inhibit the cell proliferation, and develop a safe and effective antitumor medicament. This can undoubtedly help advancing the process of the cancer treatment.

SUMMARY OF THE INVENTION

The present invention provides a novel inhibitor, which can selectively and effectively inhibit the FGF signaling and therefore inhibit the cell proliferation, and prevent or treat an FGFR kinase mediated disorder or disease, such as cancer.

The present invention provides a compound represented by general formula (I), or a pharmaceutically acceptable salt thereof, $$\text{(I)}$$

wherein:
X is CR6 or N;
Y is CR6R7 or C(=O);
Z is CR6 or N;
$R_1$ is selected from the group consisting of H, halogen, hydroxy, —$C_1$-$C_6$alkyl, —$C_1$-$C_6$alkoxy, —$C_1$-$C_6$alkylthio, —$C_3$-$C_6$cycloalkyl, halo$C_1$-$C_6$alkyl, hydroxy$C_1$-$C_6$alkyl, —$(CH_2)_n$—$NR_6R_7$, or $C_3$-$C_6$cycloalkyl or 4-7 membered heterocycloalkyl, which can be optionally substituted with one or more groups selected from the group consisting of halogen, hydroxy, —$C_1$-$C_6$alkyl, —$C_1$-$C_6$alkoxy, —$C_1$-$C_6$alkylthio, and —$NH_2$;

$R_2$ is selected from the group consisting of H, halogen, hydroxy, —$C_1$-$C_6$alkyl, —$C_1$-$C_6$alkoxy or —$C_3$-$C_6$cycloalkyl;

$R_3$, $R_4$ and $R_5$ are each independently selected from the group consisting of H, halogen, hydroxy, —$C_1$-$C_6$alkyl, —$C_1$-$C_6$alkoxy, —$C_3$-$C_6$cycloalkyl, —O—$C_3$-$C_6$cycloalkyl, —$C_1$-$C_6$alkylthio, halo$C_1$-$C_6$alkyl, hydroxy$C_1$-$C_6$alkyl, —C(=O)—$NR_6R_7$, —$NR_6R_7$, —OC(=O)$R_6$, —COOR$_6$, —$NR_6$C(=O)$R_7$, —$NR_6$COOR$_7$ and —OSO$_2R_6$;

$R_6$ and $R_7$ are each independently selected from the group consisting of H, —$C_1$-$C_6$alkyl, —$C_1$-$C_6$alkoxy, —$C_3$-$C_6$cycloalkyl or —$C_1$-$C_6$alkylthio; n is 0, 1, 2, 3 or 4.

The present invention also provides a process for preparing the compound represented by general formula (I).

The present invention also provides an alternative process for preparing the compound represented by general formula (I).

The present invention further provides a pharmaceutical composition, comprising the above compound represented by general formula (I) according to the present invention or a pharmaceutically acceptable salt thereof and a pharmaceutically acceptable carrier.

The present invention further provides the compound represented by general formula (I) or a pharmaceutically acceptable salt thereof or a pharmaceutical composition comprising the compound represented by general formula (I) or a pharmaceutically acceptable salt thereof as a medicament for preventing and/or treating FGFR kinase mediated disorder or disease.

The present invention further provides the compound represented by general formula (I) or a pharmaceutically acceptable salt thereof or a pharmaceutical composition comprising the compound represented by general formula (I) or a pharmaceutically acceptable salt thereof as a medicament for preventing and/or treating cancer.

The present invention further provides use of the compound represented by general formula (I) or a pharmaceutically acceptable salt thereof or a pharmaceutical composition comprising the compound represented by general formula (I) or a pharmaceutically acceptable salt thereof in manufacture of a medicament, wherein said medicament is useful in preventing or treating FGFR kinase mediated disorder or disease.

The present invention further provides use of the compound represented by general formula (I) or a pharmaceutically acceptable salt thereof or a pharmaceutical composition comprising the compound represented by general formula (I) or a pharmaceutically acceptable salt thereof in manufacture of a medicament, wherein said medicament is useful in preventing or treating cancer.

The present invention further provides a method of preventing or treating FGFR kinase mediated disorder or disease, wherein said method comprises administrating to a patient the compound represented by general formula (I) or a pharmaceutically acceptable salt thereof or a pharmaceutical composition comprising the compound represented by general formula (I) or a pharmaceutically acceptable salt thereof.

The present invention further provides a method of preventing or treating cancer, wherein said method comprises administrating to a patient the compound represented by general formula (I) or a pharmaceutically acceptable salt thereof or a pharmaceutical composition comprising the compound represented by general formula (I) or a pharmaceutically acceptable salt thereof.

Cancer as mentioned in the present invention includes but is not limited to multiple myeloma, myeloproliferative disease, endometrial cancer, prostate cancer, bladder cancer, lung cancer, ovarian cancer, breast cancer, gastric cancer, colorectal cancer, oral squamous cell carcinoma, squamous cell carcinoma, liver cancer, kidney cancer, colon cancer and non-small cell lung cancer, ovarian cancer, cervical cancer, pancreatic cancer, glioma, glioblastoma, mesothelioma, leukemia, lymphoma, melanoma, head and neck cancer, thyroid cancer, testicular cancer.

In a preferable embodiment of the present invention, said compound is a compound represented by formula (II),

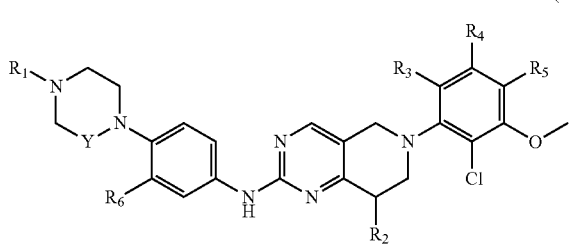

(II)

wherein $R_1$, $R_2$, $R_3$, $R_4$, $R_5$, $R_6$ and Y are defined as above.

In a preferable embodiment of the present invention, said compound is a compound represented by formula (III),

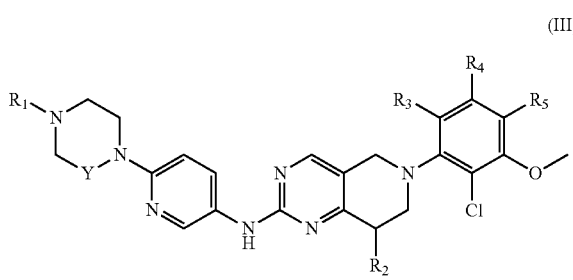

(III)

wherein $R_1$, $R_2$, $R_3$, $R_4$, $R_5$ and Y are defined as above.

In a preferable embodiment of the present invention, said compound is a compound represented by formula (IV),

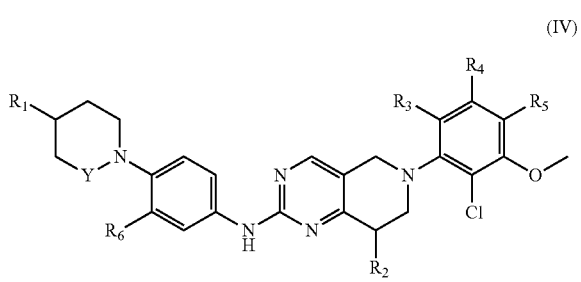

(IV)

wherein $R_1$, $R_2$, $R_3$, $R_4$, $R_5$, $R_6$ and Y are defined as above.

In a preferable embodiment of the present invention, said compound is a compound represented by formula (V),

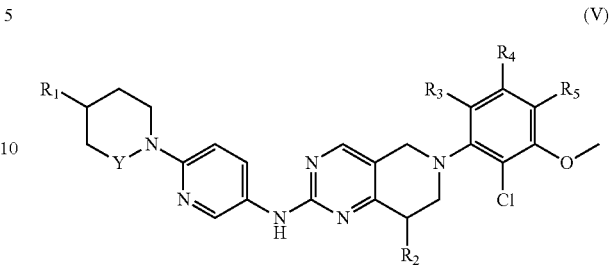

(V)

wherein $R_1$, $R_2$, $R_3$, $R_4$, $R_5$ and Y are defined as above.

In a more preferable embodiment of the present invention, in the structural formula of the compound represented by formula (II) and the compound represented by formula (IV), the substituent $R_6$ of the benzene ring is selected from the group consisting of H, —$C_1$-$C_6$alkyl or —$C_1$-$C_6$alkoxy, more preferably the substituent $R_6$ is selected from the group consisting of H, —$C_1$-$C_4$alkyl or —$C_1$-$C_4$alkoxy, and more preferably the substituent $R_6$ is H.

In another preferable embodiment of the present invention, in the compound represented by formula (I), the compound represented by formula (II), the compound represented by formula (III), the compound represented by formula (IV) or the compound represented by formula (V), Y is $CR_6R_7$, wherein $R_6$ and $R_7$ are each independently selected from the group consisting of H or —$C_1$-$C_6$alkyl, more preferably $R_6$ and $R_7$ are each independently selected from the group consisting of H or —$C_1$-$C_4$alkyl, and more preferably $R_6$ and $R_7$ are both H.

In another preferable embodiment of the present invention, in the compound represented by formula (I), the compound represented by formula (II), the compound represented by formula (III), the compound represented by formula (IV) or the compound represented by formula (V), Y is C(=O).

In another preferable embodiment of the present invention, in the compound represented by formula (I), the compound represented by formula (II), the compound represented by formula (III), the compound represented by formula (IV) or the compound represented by formula (V), $R_1$ is selected from the group consisting of H, halogen, hydroxy, —$C_1$-$C_6$alkyl, —$C_1$-$C_6$alkoxy, —$C_1$-$C_6$alkylthio, —$C_3$-$C_6$cycloalkyl, halo$C_1$-$C_6$alkyl, hydroxy$C_1$-$C_6$alkyl, and —$(CH_2)_n$—$NR_6R_7$, wherein $R_6$ and $R_7$ are each independently selected from the group consisting of H, —$C_1$-$C_6$alkyl or —$C_1$-$C_6$alkoxy, n is 0, 1, 2 or 3.

In a more preferable embodiment of the present invention, in the compound represented by formula (I), the compound represented by formula (II), the compound represented by formula (III), the compound represented by formula (IV) or the compound represented by formula (V), $R_1$ is selected from the group consisting of H, hydroxy, —$C_1$-$C_6$alkyl, —$C_1$-$C_6$alkoxy, —$C_3$-$C_6$cycloalkyl, halo$C_1$-$C_6$alkyl, hydroxy$C_1$-$C_6$alkyl, and —$(CH_2)_n$—$NR_6R_7$, wherein $R_6$ and $R_7$ are each independently selected from the group consisting of H, —$C_1$-$C_6$alkyl or —$C_1$-$C_6$alkoxy, n is 0, 1 or 2.

In a more preferable embodiment of the present invention, in the compound represented by formula (I), the compound represented by formula (II), the compound represented by formula (III), the compound represented by formula (IV) or the compound represented by formula (V), $R_1$ is selected from the group consisting of H, hydroxy, —$C_1$-$C_4$alkyl, —$C_1$-$C_4$alkoxy, —$C_3$-$C_6$cycloalkyl, halo$C_1$-$C_4$alkyl, hydroxy$C_1$-$C_4$alkyl, and —$(CH_2)_n$—$NR_6R_7$, wherein $R_6$ and $R_7$ are each independently selected from the group consisting of H, —$C_1$-$C_4$alkyl or —$C_1$-$C_4$alkoxy, n is 0, 1 or 2.

In another preferable embodiment of the present invention, in the compound represented by formula (I), the compound represented by formula (II), the compound represented by formula (III), the compound represented by formula (IV) or the compound represented by formula (V), $R_2$ is selected from the group consisting of H, halogen, hydroxy or —$C_1$-$C_6$alkyl, more preferably $R_2$ is selected from the group consisting of H, halogen, hydroxy or —$C_1$-$C_4$alkyl, more preferably $R_2$ is selected from the group consisting of H or —$C_1$-$C_4$alkyl.

In another preferable embodiment of the present invention, in the compound represented by formula (I), the compound represented by formula (II), the compound represented by formula (III), the compound represented by formula (IV) or the compound represented by formula (V), $R_3$, $R_4$ and $R_5$ are each independently selected from the group consisting of H, halogen, hydroxy, —$C_1$-$C_6$alkyl, —$C_1$-$C_6$alkoxy, —$C_3$-$C_6$cycloalkyl, —O—$C_3$-$C_6$cycloalkyl, —$C_1$-$C_6$alkylthio, halo$C_1$-$C_6$alkyl, hydroxy$C_1$-$C_6$alkyl, and —C(=O)—$NR_6R_7$, and $R_3$, $R_4$ and $R_5$ are not H at the same time, wherein $R_6$ and $R_7$ are each independently selected from the group consisting of H, —$C_1$-$C_6$alkyl or —$C_1$-$C_6$alkoxy.

In a more preferable embodiment of the present invention, in the compound represented by formula (I), the compound represented by formula (II), the compound represented by formula (III), the compound represented by formula (IV) or the compound represented by formula (V), $R_3$, $R_4$ and $R_5$ are each independently selected from the group consisting of H, halogen, hydroxy, —$C_1$-$C_6$alkyl, —$C_1$-$C_6$alkoxy, and —C(=O)—$NR_6R_7$, and $R_3$, $R_4$ and $R_5$ are not H at the same time, wherein $R_6$ and $R_7$ are each independently selected from the group consisting of H, —$C_1$-$C_6$alkyl or —$C_1$-$C_6$alkoxy.

In a more preferable embodiment of the present invention, in the compound represented by formula (I), the compound represented by formula (II), the compound represented by formula (III), the compound represented by formula (IV) or the compound represented by formula (V), $R_3$, $R_4$ and $R_5$ are each independently selected from the group consisting of H, halogen, hydroxy, —$C_1$-$C_4$alkyl, —$C_1$-$C_4$alkoxy, and —C(=O)—$NR_6R_7$, and $R_3$, $R_4$ and $R_5$ are not H at the same time, wherein $R_6$ and $R_7$ are each independently selected from the group consisting of H, —$C_1$-$C_4$alkyl or —$C_1$-$C_4$alkoxy.

In the present invention, the specific and preferable compound represented by general formula (I) or a pharmaceutically acceptable salt thereof, includes:

6-(2,6-dichloro-3,5-dimethoxyphenyl)-N-(4-(4-ethylpiperazin-1-yl)phenyl)-5,6,7,8-tetrahydropyrido[4,3-d]pyrimidin-2-amine;

6-(2,6-dichloro-3,5-dimethoxyphenyl)-N-(4-(4-(2,2,2-trifluoroethyl)piperazin-1-yl)phenyl)-5,6,7,8-tetrahydropyrido[4,3-d]pyrimidin-2-amine;

2-(4-(4-(6-(2,6-dichloro-3,5-dimethoxyphenyl)-5,6,7,8-tetrahydropyrido[4,3-d]pyrimidin-2-ylamino)phenyl)piperazin-1-yl)ethanol;

6-(2,6-dichloro-3,5-dimethoxyphenyl)-N-(4-(4-(2-(dimethylamino)ethyl)piperazin-1-yl)phenyl)-5,6,7,8-tetrahydropyrido[4,3-d]pyrimidin-2-amine;

6-(2,6-dichloro-3,5-dimethoxyphenyl)-N-(4-(4-(dimethylamino)piperidin-1-yl)phenyl)-5,6,7,8-tetrahydropyrido[4,3-d]pyrimidin-2-amine;

6-(2,6-dichloro-3,5-dimethoxyphenyl)-N-(4-(4-cyclopropylpiperazin-1-yl)phenyl)-5,6,7,8-tetrahydropyrido[4,3-d]pyrimidin-2-amine;

1-(4-(6-(2,6-dichloro-3,5-dimethoxyphenyl)-5,6,7,8-tetrahydropyrido[4,3-d]pyrimidin-2-ylamino)phenyl-4-ethylpiperazin-2-one;

6-(2,6-dichloro-3,5-dimethoxyphenyl)-N-(6-(4-ethylpiperazin-1-yl)pyridin-3-yl)-5,6,7,8-tetrahydropyrido[4,3-d]pyrimidin-2-amine;

6-(2,6-dichloro-3,5-dimethoxyphenyl)-N-(6-(4-(dimethylamino)piperidin-1-yl)pyridin-3-yl)-5,6,7,8-tetrahydropyrido[4,3-d]pyrimidin-2-amine;

6-(2,6-dichloro-3,5-dimethoxyphenyl)-N-(4-(4-ethylpiperazin-1-yl)-3-methoxyphenyl)-5,6,7,8-tetrahydropyrido[4,3-d]pyrimidin-2-amine;

4-chloro-3-(2-(6-(4-ethylpiperazin-1-yl)pyridin-3-ylamino)-7,8dihydropyrido[4,3-d]pyrimidin-6(5H)-yl)-5-methoxy-N-methylbenzamide;

4-chloro-3-(2-(6-(4-ethylpiperazin-1-yl)pyridin-3-ylamino)-7,8dihydropyrido[4,3-d]pyrimidin-6(5H)-yl)-N,5-dimethoxybenzamide;

4-chloro-3-(2-(4-(4-(dimethylamino)piperazin-1-yl)phenylamino)-7,8dihydropyrido[4,3-d]pyrimidin-6(5H)-yl)-5-methoxy-N-methylbenzamide;

2-(4-(5-(6-(2,6-dichloro-3,5-dimethoxyphenyl)-5,6,7,8-tetrahydropyrido[4,3-d]pyrimidin-2-ylamino)pyridin-2-yl)piperazin-1-yl)ethanol;

6-(2-fluoro-6-chloro-3,5-dimethoxyphenyl)-N-(4-(4-(dimethylamino)piperidin-1-yl)phenyl)-5,6,7,8-tetrahydropyrido[4,3-d]pyrimidin-2-amine.

The present invention further provides a process for preparing a compound represented by general formula (I), as shown in the following scheme I, comprising the following steps:

SCHEME I

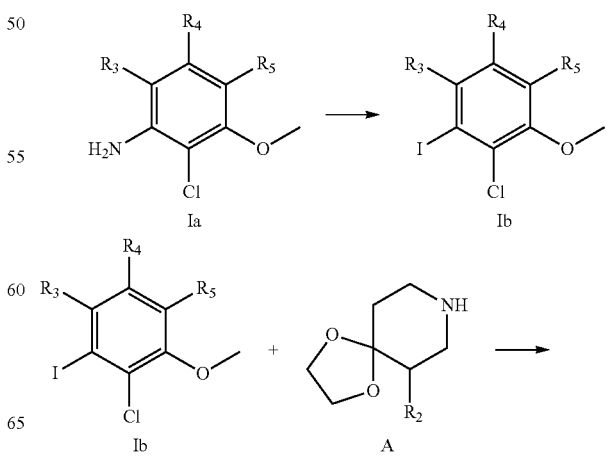

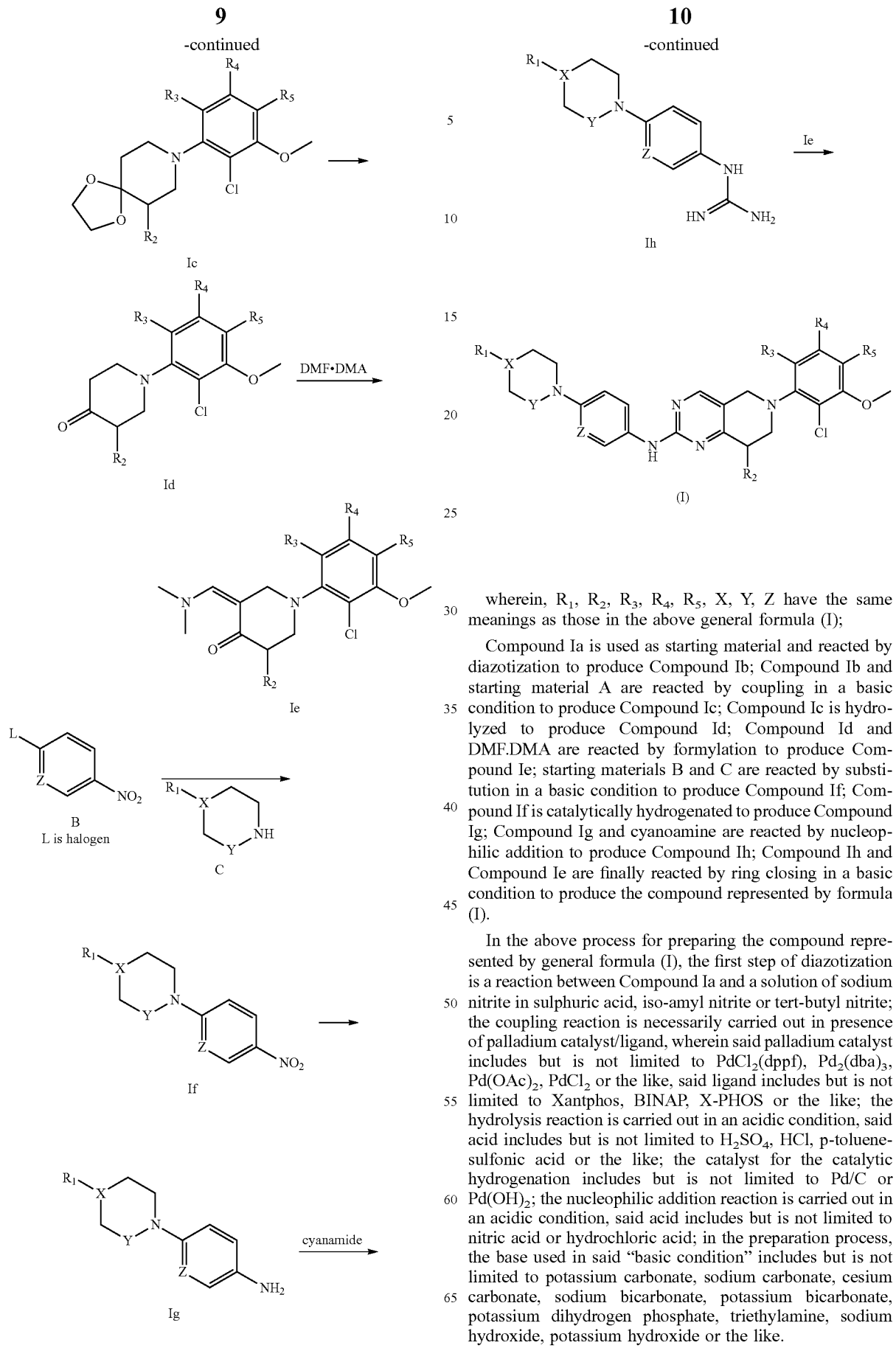

wherein, $R_1$, $R_2$, $R_3$, $R_4$, $R_5$, X, Y, Z have the same meanings as those in the above general formula (I);

Compound Ia is used as starting material and reacted by diazotization to produce Compound Ib; Compound Ib and starting material A are reacted by coupling in a basic condition to produce Compound Ic; Compound Ic is hydrolyzed to produce Compound Id; Compound Id and DMF.DMA are reacted by formylation to produce Compound Ie; starting materials B and C are reacted by substitution in a basic condition to produce Compound If; Compound If is catalytically hydrogenated to produce Compound Ig; Compound Ig and cyanoamine are reacted by nucleophilic addition to produce Compound Ih; Compound Ih and Compound Ie are finally reacted by ring closing in a basic condition to produce the compound represented by formula (I).

In the above process for preparing the compound represented by general formula (I), the first step of diazotization is a reaction between Compound Ia and a solution of sodium nitrite in sulphuric acid, iso-amyl nitrite or tert-butyl nitrite; the coupling reaction is necessarily carried out in presence of palladium catalyst/ligand, wherein said palladium catalyst includes but is not limited to $PdCl_2(dppf)$, $Pd_2(dba)_3$, $Pd(OAc)_2$, $PdCl_2$ or the like, said ligand includes but is not limited to Xantphos, BINAP, X-PHOS or the like; the hydrolysis reaction is carried out in an acidic condition, said acid includes but is not limited to $H_2SO_4$, HCl, p-toluenesulfonic acid or the like; the catalyst for the catalytic hydrogenation includes but is not limited to Pd/C or $Pd(OH)_2$; the nucleophilic addition reaction is carried out in an acidic condition, said acid includes but is not limited to nitric acid or hydrochloric acid; in the preparation process, the base used in said "basic condition" includes but is not limited to potassium carbonate, sodium carbonate, cesium carbonate, sodium bicarbonate, potassium bicarbonate, potassium dihydrogen phosphate, triethylamine, sodium hydroxide, potassium hydroxide or the like.

The present invention further provides an alternative process for preparing a compound represented by general formula (I), as shown in the following scheme II, comprising the following steps:

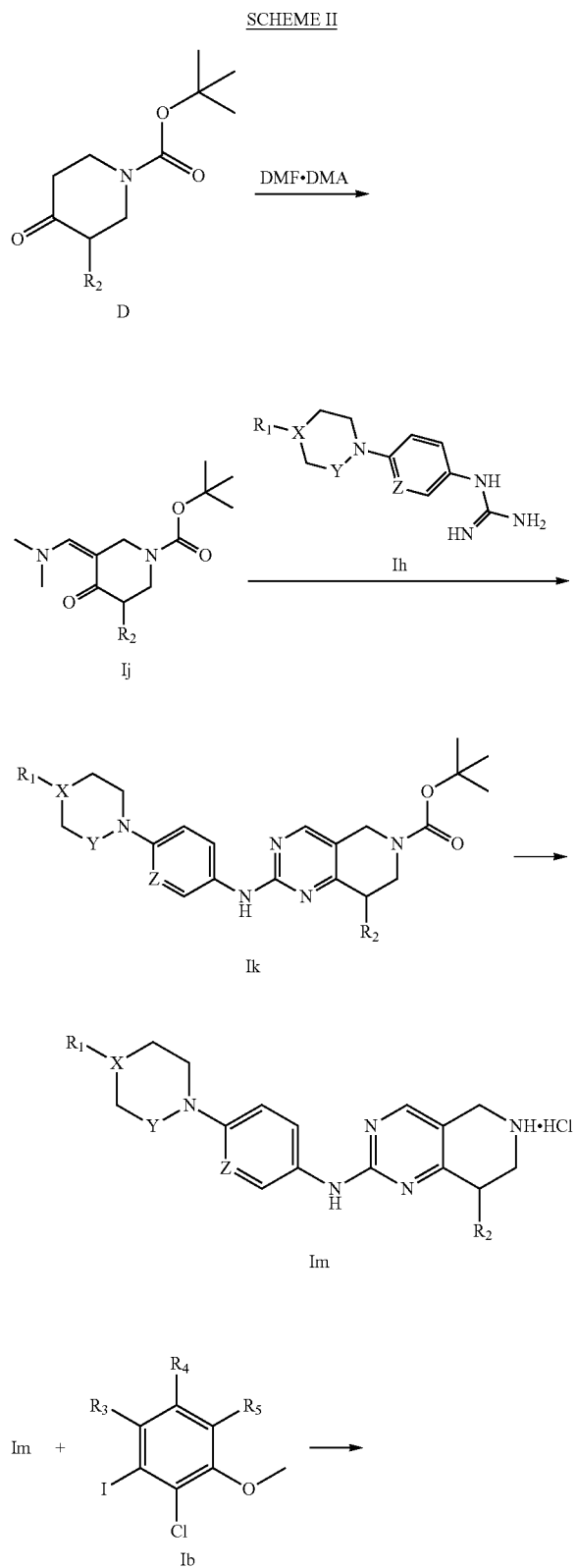

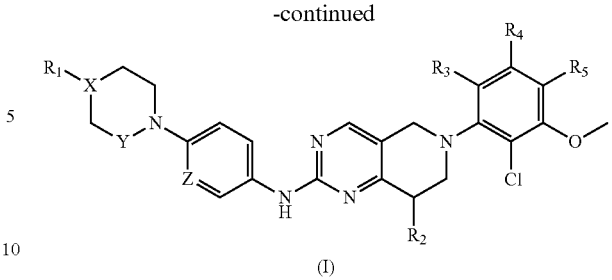

wherein, $R_1$, $R_2$, $R_3$, $R_4$, $R_5$, X, Y, Z have the same meanings as those in the above general formula (I);

Starting compound D and DMF·DMA are reacted by formylation to produce Compound Ij; Compound Ij and Compound Ih are reacted by ring closing in a basic condition to produce Compound Ik; Compound Ik is deprotected in an acidic condition to form a salt and produce Compound Im; Compound Im and Compound Ib are finally reacted by coupling in a basic condition to produce the compound represented by formula (I).

In the above alternative process for preparing the compound represented by general formula (I), the acid used in the deprotection reaction includes but is not limited to $H_2SO_4$, HCl, trifluoroacetic acid or like; the coupling reaction is necessarily carried out in presence of palladium catalyst/ligand, wherein said palladium catalyst includes but is not limited to $PdCl_2(dppf)$, $Pd_2(dba)_3$, $Pd(OAc)_2$, $PdCl_2$ or like, said ligand includes but is not limited to Xantphos, BINAP, X-PHOS or the like; in the preparation process, the base used in said "basic condition" includes but is not limited to potassium carbonate, sodium carbonate, cesium carbonate, sodium bicarbonate, potassium bicarbonate, potassium dihydrogen phosphate, triethylamine, sodium hydroxide, potassium hydroxide or like.

In the above preparation processes, the used abbreviations for the agents have the following meanings:

| | |
|---|---|
| $PdCl_2(dppf)$ | [1,1'-Bis(diphenylphosphino)ferrocene]dichloropalladium |
| $Pd_2(dba)_3$ | Tris(dibenzylideneacetone)dipalladium |
| $Pd(OAc)_2$ | Palladium acetate |
| $PdCl_2$ | Palladium chloride |
| Xantphos | 4,5-Bis(diphenylphosphino)-9,9-dimethylxanthene |
| BINAP | 2,2'-Bis(diphenylphosphino)-1,1'-binaphthyl |
| X-PHOS | 2-Dicyclohexylphosphino-2',4',6'-triisopropylbiphenyl |
| DMF·DMA | N,N-dimethylformamide dimethyl acetal |
| DMF | N,N-dimethylformamide |
| MsCl | Methylsulfonyl chloride |
| DCM | Dichloromethane |
| BOC- | Tert-butoxycarbonyl |
| EtOH | Ethanol |
| $Et_3N$ | Triethylamine |
| THF | Tetrahydrofuran |
| NaOAc | Sodium acetate |
| Con.HCl | Concentrated hydrochloric acid |
| Dioxane | Dioxane |
| oxalyldichloride | Oxalyl dichloride |
| reflux | Reflux |
| RT | Room temperature |

In the present invention, the term "halogen" means fluoro, chloro, bromo, iodo and the like, preferably fluoro, chloro and bromo, and more preferably chloro.

In the present invention, —$C_1$-$C_6$alkyl refers to an alkyl having 1-6 carbon atoms, and includes but is not limited to, for example, methyl, ethyl, propyl, iso-propyl, butyl, iso-butyl, sec-butyl, tert-butyl, pentyl, hexyl or the like, preferably $C_1$-$C_4$alkyl referring to an alkyl having 1-4 carbon atoms, and includes but is not limited to, methyl, ethyl, propyl, iso-propyl, butyl, iso-butyl, sec-butyl and tert-butyl, more preferably methyl, ethyl, propyl, iso-propyl or butyl.

In the present invention, —$C_1$-$C_6$alkoxy refers to an alkoxy having 1-6 carbon atoms, and includes but is not limited to, for example, methyloxy, ethyloxy, propyloxy, iso-propyloxy, butyloxy, iso-butyloxy, sec-butyloxy, tert-butyloxy, pentyloxy, hexyloxy or the like, preferably —$C_1$-$C_4$alkoxy referring to an alkoxy having 1-4 carbon atoms, and includes but is not limited to, methyloxy, ethyloxy, propyloxy, iso-propyloxy, butyloxy, iso-butyloxy, sec-butyloxy and tert-butyloxy, more preferably methyloxy, ethyloxy, propyloxy, iso-propyloxy or butyloxy.

In the present invention, —$C_1$-$C_6$alkylthio refers to an alkylthio having 1-6 carbon atoms, and includes but is not limited to, for example, methylthio, ethylthio, propylthio, iso-propylthio, butylthio, iso-butylthio, sec-butylthio, tert-butylthio, pentylthio, hexylthio or the like, preferably —$C_1$-$C_4$alkylthio referring to an alkylthio having 1-4 carbon atoms, and includes but is not limited to, methylthio, ethylthio, propylthio, iso-propylthio, butylthio, iso-butylthio, sec-butylthio and tert-butylthio, more preferably methylthio, ethylthio, propylthio, iso-propylthio or butylthio.

In the present invention, $C_3$-$C_6$cycloalkyl refers to a mono-valent group derived from monocyclic saturated or partially unsaturated aliphatic carbocyclic compounds, and includes but is not limited to cyclopropyl, cyclobutyl, cyclopentyl, cyclohexyl, cyclopropenyl, cyclobutenyl, cyclopentenyl, cyclohexenyl, preferably cyclopropyl, cyclobutyl, cyclopentyl, cyclohexyl.

In the present invention, $C_3$-$C_6$cycloalkyl in —O—$C_3$-$C_6$cycloalkyl is defined as above, and —O—$C_3$-$C_6$cycloalkyl includes but is not limited to —O-cyclopropyl, —O-cyclobutyl, —O-cyclopentyl, —O-cyclohexyl.

In the present invention, halo$C_1$-$C_6$alkyl refers to $C_1$-$C_6$alkyl as defined herein that is substituted with one or more halogen atoms, preferably 1-8 halogen atoms, preferably halo$C_1$-$C_4$alkyl referring to $C_1$-$C_4$alkyl as defined herein that is substituted with one or more halogen atoms, preferably 1-5 halogen atoms, and includes but is not limited to trifluoromethyl, trifluoroethyl, difluoromethyl, 1-chloro-2-fluoroethyl and the like, more preferably trifluoroethyl.

In the present invention, hydroxy$C_1$-$C_6$alkyl refers to $C_1$-$C_6$alkyl as defined herein, in which one or more hydrogen atoms are substituted with hydroxy, including monohydroxy$C_1$-$C_6$alkyl and polyhydroxy$C_1$-$C_6$alkyl, with one, two, three or more hydrogen atoms substituted with hydroxy, preferably hydroxy$C_1$-$C_4$alkyl, including monohydroxy$C_1$-$C_4$alkyl and polyhydroxy$C_1$-$C_4$alkyl, which includes but is not limited to hydroxymethyl, hydroxyethyl or hydroxypropyl.

In the present invention, the term "4-7 membered heterocycloalkyl" means a monovalent monocyclic group, which is saturated or partially unsaturated (but not aromatic) and contains 4-7 ring members, wherein 1-4 ring heteroatom(s) is/are selected from a group consisting of O, S and N, and the remaining ring atoms are carbon. Said heterocycloalkyl includes but is not limited to azetidinyl, oxetanyl, pyrrolidinyl, piperidyl, morpholinyl, piperazinyl, tetrahydropyranyl, pyrazolidinyl, pyrazolinyl, imidazolinyl, imidazolidinyl, [1,3]dioxolane (dioxolane), dihydropyridinyl, tetrahydropyridinyl, hexahydropyridinyl, oxazolinyl, oxazolidinyl, iso-oxazolidinyl, thiazolinyl, thiazolidinyl, tetrahydrothiazolyl, iso-tetrahydrothiazolyl, tetrahydrofuryl and the like, preferably azetidinyl, oxetanyl, pyrrolidinyl, piperidyl, morpholinyl or piperazinyl.

The present invention also includes the pharmaceutically acceptable salt of the compound represented by formula (I). The term "pharmaceutically acceptable salt" means relatively nontoxic acid addition salts or base addition salts of the compound of the present invention. Said acid addition salts are the salts formed between the compound represented by formula (I) of the present invention and suitable inorganic acids or organic acids. Said salts may be prepared during the final separation and purification processes of the compounds, or may be prepared through the reaction of purified compound represented by formula (I) in the form of free base thereof and suitable organic acids or inorganic acids. Representative acid addition salts include hydrobromic acid salt, hydrochloric acid salt, sulfate, bisulfate, sulfite, acetate, oxalate, valerate, oleate, palmate, stearate, laurate, borate, benzoate, lactate, phosphate, hydrogen phosphate, carbonate, bicarbonate, toluate, citrate, maleate, fumarate, succinate, tartrate, benzoate, mesylate, p-tosylate, glyconate, lactobionate and laurylsulfonate and the like. Said base addition salts are the salts formed between the compound represented by formula (I) and suitable inorganic bases or organic bases, for example including the salts formed with alkali metals, alkaline earth metals, quaternary ammonium cations, such as sodium salts, lithium salts, potassium salts, calcium salts, magnesium salts, tetramethylammonium salts, tetraethylammonium salt and the like; amine salts, including the salts formed with ammonia ($NH_3$), primary amines, secondary amines or tertiary amines, such as methylamine salts, dimethylamine salts, trimethylamine salts, triethylamine salts, ethylamine salts and the like.

The compound represented by formula (I) of the present invention or a pharmaceutically acceptable salt thereof can be administered to mammals, such as human, and administrated orally, rectally, parenterally (intravenously, intramuscularly or subcutaneously), topically (such as in the form of powders, ointments or drops), or intratumorally.

The compound of the present invention or a pharmaceutically acceptable salt thereof can be formulated into the solid dosage forms for oral administration, which includes but is not limited to capsules, tablets, pills, powders and granules and the like. In these solid dosage forms, the compound represented by formula (I) of the present invention as active ingredient is admixed with at least one conventional inert excipients (or carriers), such as sodium citrate or dicalcium phosphate, or admixed with the following ingredients: (1) fillers or extenders, such as, starch, lactose, sucrose, glucose, mannitol and silicic acid and the like; (2) adhesives, such as, hydroxymethylcellulose, alginate, gelatin, polyvinyl pyrrolidine, sucrose and acacia and the like; (3) humectants, such as, glycerol and the like; (4) disintegrating agents, such as, agar, calcium carbonate, potato starch or tapioca starch, alginic acid, certain composite silicate and sodium carbonate and the like; (5) retarding solvents, such as paraffin wax and the like; (6) absorption accelerators, such as, quaternary ammonium compounds and the like; (7) moistening agents, such as cetanol and glyceryl monostearate and the like; (8) absorbents, such as, kaolin and the like; and (9) lubricants, such as, talc, calcium stearate, magnesium stearate, solid polyethylene glycol, sodium dodecyl sulphate and the like, or mixtures thereof. Capsules, tablets and pills may also comprise buffers.

Said solid dosage forms such as tablets, sugar pills, capsules, pills and granules can also by coated or microencapsulated by coatings and shell materials such as enteric coatings and other materials well known in the art. They may comprise opacifying agents, and the release of active ingredients in these compositions may be carried out in a certain portion of digestive tube in a retarded manner. The examples for embedding components that may be adopted are polymers and waxes. If necessary, active ingredients can also be formulated into the form of microcapsules with one or more of the above excipients.

The compound represented by formula (I) of the present invention or a pharmaceutically acceptable salt thereof can be formulated into liquid dosage forms for oral administration, including but not limited to pharmaceutically acceptable emulsions, solutions, suspensions, syrups and tinctures and the like. Besides the compound represented by formula (I) or a pharmaceutically acceptable salt thereof as active ingredient, the liquid dosage forms may comprise inert diluents customarily used in the art, such as water and other solvents, solubilizers and emulsifiers, such as, ethanol, isopropyl alcohol, ethyl carbonate, ethyl acetate, propylene glycol, 1,3-butanediol, dimethyl formamide, and oils, especially cottonseed oil, peanut oil, corn germ oil, olive oil, castor oil and sesame oil and the like or mixtures of these materials and the like. Besides these inert diluents, the liquid dosage forms of the present invention may also comprise conventional auxiliaries, such as moistening agents, emulsifiers and suspending agents, sweeting agents, flavoring agents and fragrances and the like.

Besides the compound represented by formula (I) of the present invention or a pharmaceutically acceptable salt thereof, said suspension can contain a suspending agent, such as ethoxylated isostearyl alcohol, polyoxyethylene sorbitol and sorbitan ester, microcrystalline cellulose, aluminium methoxide and agar and the like or mixtures of these materials.

The compound represented by formula (I) of the present invention or a pharmaceutically acceptable salt thereof can be formulated into dosage forms for parenteral injection, including but not limited to physiologically acceptable sterile aqueous or anhydrous solutions, dispersions, suspensions or emulsions, and sterile powder for re-dissolving into sterile injectable solutions or dispersions. Suitable carriers, diluents, solvents or excipients include water, ethanol, polyhydric alcohol and suitable mixtures thereof.

The compound of the present invention or a pharmaceutically acceptable salt thereof can also be formulated into dosage forms for topical administration, including but not limited to ointments, powders, suppositories, drops, propellants and inhalants and the like. The compound represented by formula (I) of the present invention or a pharmaceutically acceptable salt thereof as active ingredient is admixed together with physiologically acceptable carriers and optional preservatives, buffers, or if necessary, propellants, under sterile condition.

The present invention also provides a pharmaceutical composition containing the compound represented by formula (I) of the present invention or a pharmaceutically acceptable salt thereof as active ingredient, and pharmaceutically acceptable carriers, excipients or diluents. When preparing the pharmaceutical composition, the compound represented by formula (I) of the present invention or a pharmaceutically acceptable salt thereof is generally admixed with pharmaceutically acceptable carriers, excipients or diluents.

By conventional preparation methods, the composition of the present invention may be formulated into conventional pharmaceutical preparations, such as tablets, pills, capsules, powder, granules, emulsions, suspensions, dispersions, solutions, syrups, elixirs, ointments, drops, suppositories, inhalants, propellants and the like.

The present invention further provides a method of treating the FGFR kinase mediated disorder or disease such as cancer. Said cancer is treated or alleviated by inhibiting the FGFR activity. The treatment method comprises a step of administrating to a patient in need thereof the compound represented by formula (I) of the present invention or a pharmaceutically acceptable salt thereof in an amount of 0.05-50 mg/kg body weight/day, preferably 0.1-45 mg/kg body weight/day, more preferably 0.5-35 mg/kg body weight/day.

The compound represented by formula (I) of the present invention or a pharmaceutically acceptable salt thereof may be administered alone or in combination with other pharmaceutically acceptable therapeutic agents. The therapeutic agents include but are not limited to: (i) other antiproliferative/antineoplastic drugs and combinations thereof, as used in medical oncology, such as alkylating agents (for example cis platin, oxaliplatin, carboplatin and the like); antimetabolites (for example gemcitabine and the like); antitumor antibiotics (for example doxorubicin and the like); antimitotic agents (for example vinca alkaloids like vincristine, vinblastine, and taxoids like taxol and the like); and topoisomerase inhibitors (for example epipodophyllotoxins like etoposide and the like); (ii) cytostatic agents such as anti-oestrogens (for example tamoxifen and the like), antiandrogens (for example bicalutamide and the like), progestogens (for example megestrol acetate) and the like; (iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), metalloproteinase inhibitors like marimastat, and the like; (iv) inhibitors of growth factor function, for example, growth factor antibodies and growth factor receptor antibodies such as the anti erbB2 antibody trastuzumab [Herceptin™], tyrosine kinase inhibitors, for example inhibitors of the epidermal growth factor family (for example gefitinib), erbB2 tyrosine kinase inhibitors such as lapatinib, inhibitors of the hepatocyte growth factor family, inhibitors of the platelet-derived growth factor family such as imatinib, inhibitors of cell signaling through MEK and/or AKT kinases, inhibitors of the hepatocyte growth factor family, c-kit inhibitors, abl kinase inhibitors, IGF receptor (insulin-like growth factor) kinase inhibitors and the like; or (v) antiangiogenic agents such as those which inhibit the effects of vascular endothelial growth factor, for example bevacizumab (Avastin™), vatalanib (PTK787, WO 98/35985), sunitinib (SU11248, WO 01/60814) and the like. Said combination includes not only the combination of the compound represented by formula (I) of the present invention with another active ingredient but also the combination of the compound of the present invention with two or more other active ingredients.

The assay demonstrates that the compound represented by general formula (I) of the present invention has an effect of inhibiting the proliferation of cancer cells, and can be useful in treating cancers and preparing a medicament for treating cancers. The pharmacodynamic action of the compound of the present invention in terms of inhibiting the proliferation of cancer cells may be determined by conventional methods. One preferable evaluation method is MTT (Thiazolyl Blue) cell activity assay, in which the change in optical absorption value generated after the drug has acted on the cancer cells is measured, and the inhibition ratio of a drug against the proliferation of cancer cells is calculated.

Inhibition ratio (%)=[(blank control OD−inhibitor OD)/blank control OD]×100%

Blank control OD: the OD value of the well of normally grew cells without the action of a drug.

Inhibitor OD: the OD value of the well of cells with the action of the added compounds to be screened.

The median inhibitory concentration ($IC_{50}$) value is obtained by the software GraphPad Prism 5.0 by the 4-parameter logistic curve fit calculation. Each experiment is repeated three times, and the average $IC_{50}$ value for three experiments is used as the final index for the inhibitory ability.

The good inhibition effect of the compound of the present invention on the growth of the transplantation tumor can be demonstrated through an animal assay. The pharmacodynamic action of the compound of the present invention in terms of inhibiting the growth of transplantation tumor in animal may be assayed by conventional methods. One preferable evaluation method involves the inhibitory effect on the growth of subcutaneously transplantation tumor of human bladder cancer RT112/84-bearing nude mice. The experimental method is as follows: $5\times10^6$ human bladder cancer RT112/84 cells are inoculated to nude mice subcutaneously at the right side of the back thereof, and each mouse is inoculated with 0.1 ml. After the tumors grow to 100-150 mm³ on average, the animals are divided into groups randomly according to the tumor size and the animal weight. The test compounds are administered by intragastric administration in certain dosages, and solvent control groups are administered with an equal amount of solvent by intragastric administration, wherein the administration is performed once or twice per day for a continuous period of 14 days. During the entire experimental process, the animal weight and the tumor size are measured twice per week, so as to observe whether or not the toxic reaction occurs.

The tumor volume is calculated as follows:

Tumor volume (mm³)=0.5×(Tumor major diameter× Tumor minor diameter²)

Body weight change rate (%)=measured body weight/body weight before administration× 100%.

Figure 1:
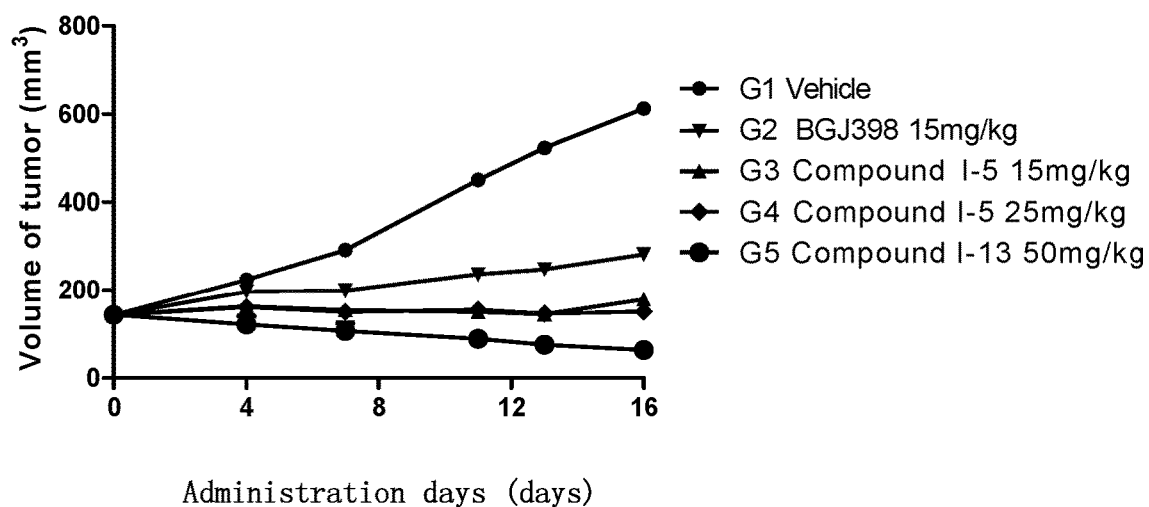
FIG. 1 is the tumor volume curve for subcutaneously transplantation tumor of human bladder cancer RT112/84-bearing nude mice for the Compounds I-5 and I-13 of the present invention and BGJ398 at their respective administration dosages.

The present invention will be further illustrated hereinafter in connection with specific Examples. It should be understood that these Examples are only used to illustrate the present invention by the way of examples without limiting the scope thereof. In the following Examples, the experimental methods without specifying conditions are generally performed according to conventional conditions or based on the conditions recommended by the manufacturer. The parts and percentages are the parts and percentages by weight respectively, unless otherwise specified.

DETAILED DESCRIPTION OF THE INVENTION

I. Example for Preparing the Compounds of the Present Invention

Example 1

6-(2,6-dichloro-3,5-dimethoxyphenyl)-N-(4-(4-ethylpiperazin-1-yl)phenyl)-5,6,7,8-tetrahydropyrido[4,3-d]pyrimidin-2-amine (I-1)

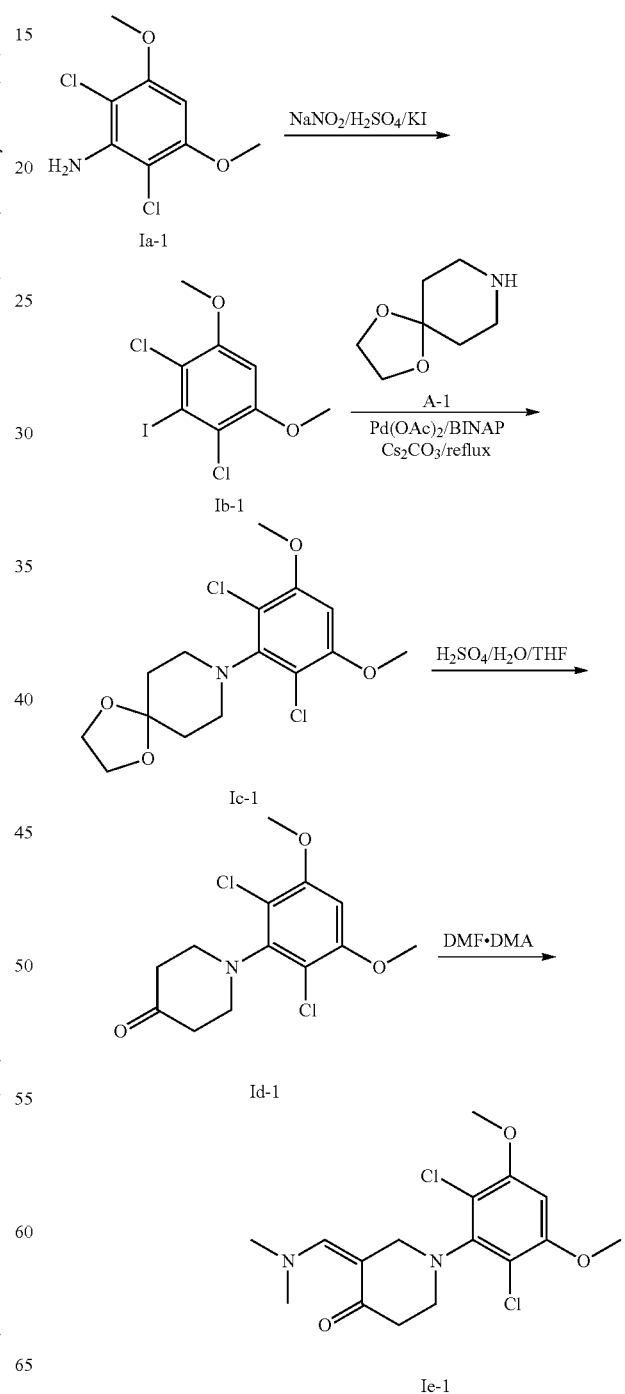

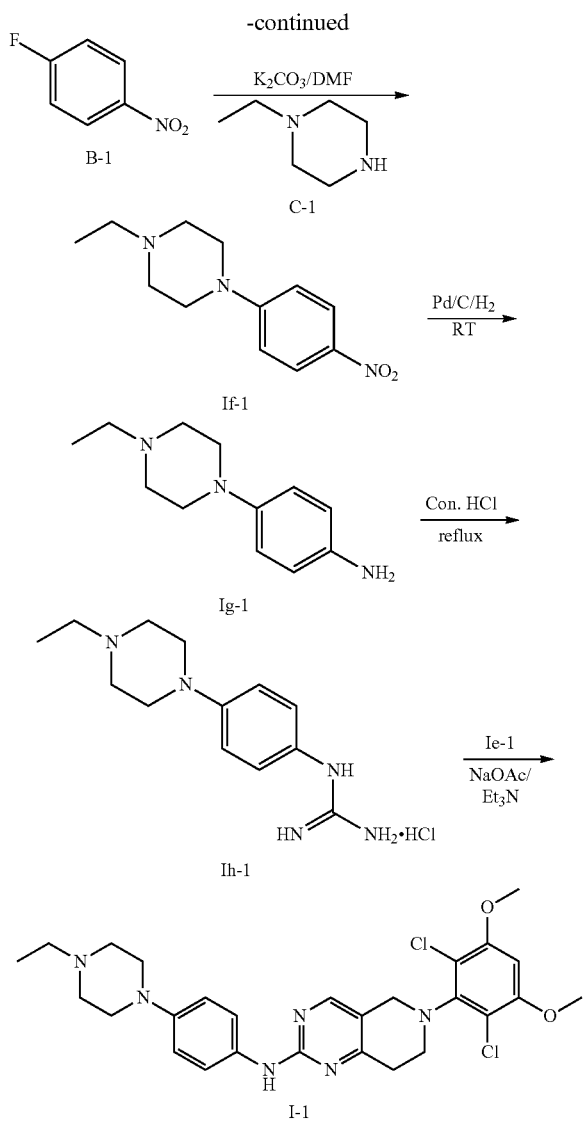

According to scheme I, to a 250-mL flask were added Compound Ia-1, i.e. 2,6-dichloro-3,5-dimethoxyaniline (10 mmol) and AcOH (24 ml), and added dropwisely under an ice-bath a solution of sodium nitrite (15 mmol) in sulphuric acid (5.8 ml). The mixture was stirred at 25° C. until the solution became clear. The resulting dark yellow solution was poured into 150 ml of an ice-water, and urea (6 mmol) was added. The mixture was stirred and filtered. An aqueous solution of potassium iodide (15 mmol) was added to the above dark-yellow solution. The mixture was heated at 85° C. for 2 hours, and cooled to room temperature. NaHSO3 (3.4 mmol) was added, and the mixture was stirred for 10 minutes. The resulting yellow solid was filtered, dried, and separated by column chromatography to produce Compound Ib-1 (8 mmol). Compound Ib-1 (4 mmol), and Compound A-1, i.e. 4-piperidinone ethylene ketal (6 mmol) were dissolved in 50 ml toluene, and palladium acetate (0.4 mmol), BINAP (0.48 mmol), and cesium carbonate (18 mmol) were added. The mixture was refluxed under the nitrogen protection for 3 days, and separated by column chromatography to produce Compound Ic-1. Compound Ic-1 (2.5 mmol) was dissolved in 10 ml THF, and 10% aqueous $H_2SO_4$ solution (10 ml) was added. The mixture was heated at 60° C. overnight, and separated by column chromatography to produce Compound Id-1. Compound Id-1 (1.0 mmol) was dissolved in 10 ml dioxane, and DMF.DMA (6.0 mmol) and triethylamine (1.0 mmol) were added. The mixture was refluxed under the nitrogen protection for 2 days, and separated by thin layer chromatography to produce Compound Ie-1. Compound B-1, i.e., 1-fluoro-4-nitrobenzene (10 mmol) was dissolved in 20 ml DMF, and C-1, i.e., N-ethylpiperazine (11 mmol), and potassium carbonate (30 mmol) were added. The mixture was reacted at 70° C. overnight. After cooling, the mixture was poured into ice-water, and filtered to produce Compound If-1. Compound If-1 (10 mmol) was dissolved in 20 ml methanol or ethanol, and palladium/carbon (1 mmol) was added. The mixture was hydrogenated at room temperature for 7 hours. The mixture was separated by column chromatography to produce Compound Ig-1. Compound Ig-1 (2.6 mmol) was dissolved in 10 ml dioxane, and cyanoamine (2.73 mmol), and concentrated hydrochloric acid (3.9 mmol) were added. The mixture was stirred under reflux overnight to produce Compound Ih-1. Compound Ie-1 (1 mmol) and Compound Ih-1 (1.05 mmol) were dissolved in 8 ml ethanol, and sodium acetate (2 mmol) and triethylamine (1.05 mmol) were added. The mixture was stirred under flux for 7 hours, ethanol concentrated, and water and dichloromethane were added. The organic phase was separated, dried over anhydrous sodium sulphate, and separated by thin layer chromatography to produce Compound I-1 (0.1 mmol) in a yield of 10%.

H1-NMR (deuterated MeOH): δ8.11 (s, 1H), δ7.56 (d, 2H), δ6.99 (d, 2H), δ6.72 (s, 1H), δ4.25 (s, 2H), δ3.93 (s, 6H), δ3.56 (t, 2H), δ3.23 (m, 4H), δ2.92 (t, 2H), δ2.8 (m, 4H), δ2.64 (m, 3H), δ1.2 (t, 3H). ESI(+) m/z: 543

Example 2

6-(2,6-dichloro-3,5-dimethoxyphenyl)-N-(4-(4-(2,2,2-trifluoroethyl)piperazin-1-yl)phenyl)-5,6,7,8-tetrahydropyrido[4,3-d]pyrimidin-2-amine (I-2)

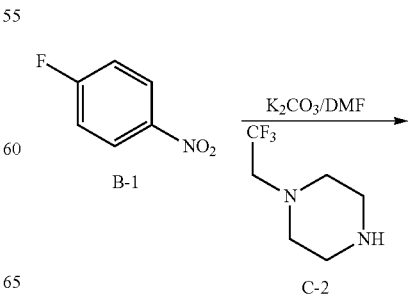

21
-continued

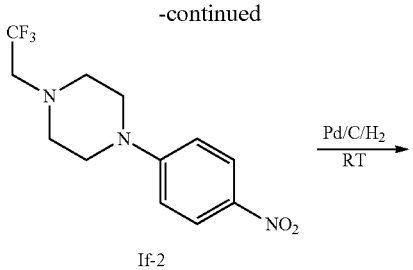

If-2

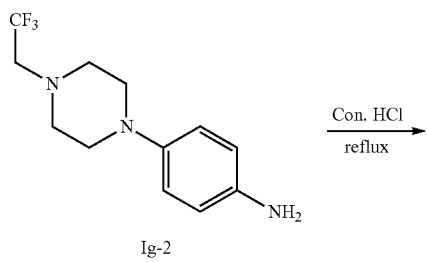

Ig-2

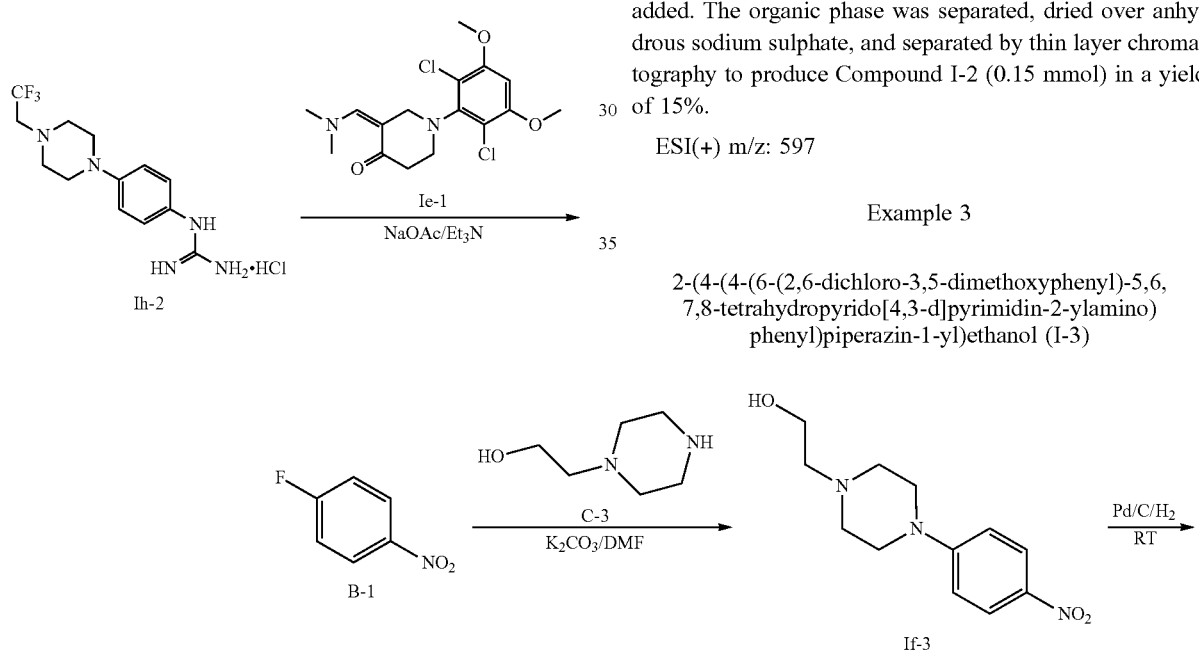

22
-continued

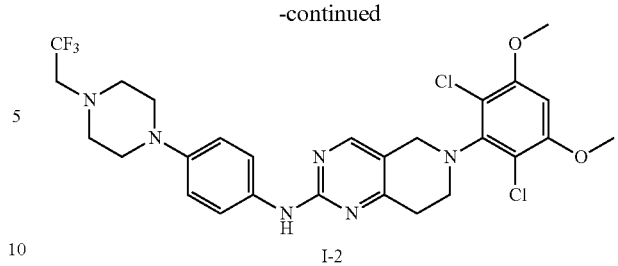

I-2

With reference to the procedure of Example 1, 2,6-dichloro-3,5-dimethoxyaniline, 4-piperidinone ethylene ketal, 1-trifluoroethylpiperazine and 1-fluoro-4-nitrobenzene were used as starting materials to synthesize and produce Compound Ih-2. Compound Ie-1 (1 mmol) and Compound Ih-2 (1.05 mmol) were dissolved in 8 ml ethanol, and sodium acetate (2 mmol) and triethylamine (1.05 mmol) were added. The mixture was stirred under flux for 7 hours, ethanol concentrated, and water and dichloromethane were added. The organic phase was separated, dried over anhydrous sodium sulphate, and separated by thin layer chromatography to produce Compound I-2 (0.15 mmol) in a yield of 15%.

ESI(+) m/z: 597

Example 3

2-(4-(4-(6-(2,6-dichloro-3,5-dimethoxyphenyl)-5,6,7,8-tetrahydropyrido[4,3-d]pyrimidin-2-ylamino)phenyl)piperazin-1-yl)ethanol (I-3)

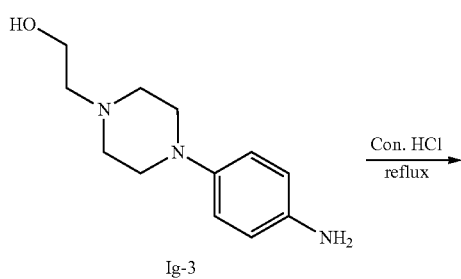

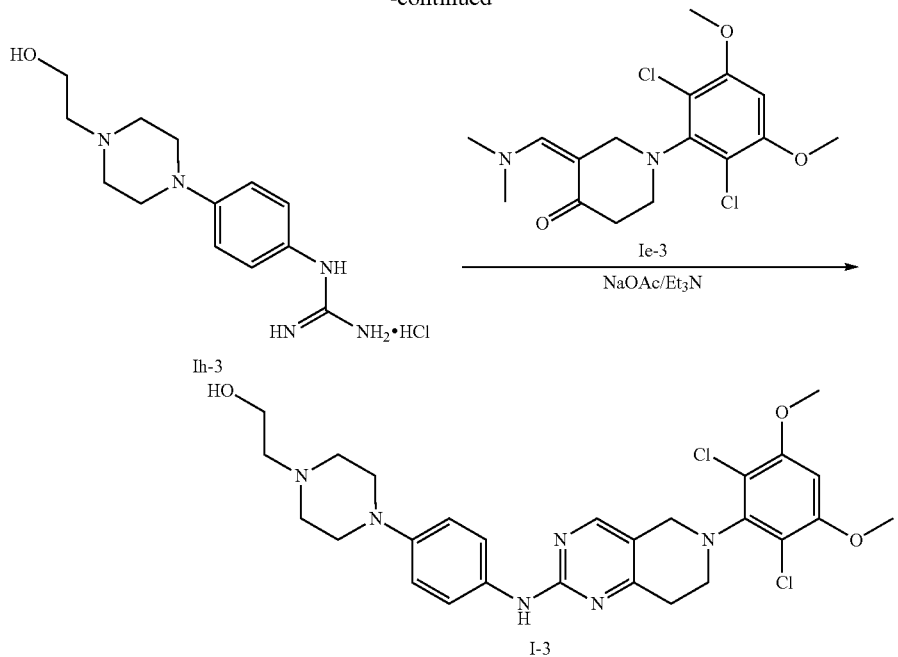

With reference to the procedure of Example 1, 2,6-dichloro-3,5-dimethoxyaniline, 4-piperidinone ethylene ketal, 1-piperazineethanol and 1-fluoro-4-nitrobenzene were used as starting materials to synthesize and produce Compound Ih-3. Compound Ie-1 (1 mmol) and Compound Ih-3 (1.05 mmol) were dissolved in 8 ml ethanol, and sodium acetate (2 mmol) and triethylamine (1.05 mmol) were added. The mixture was stirred under flux for 7 hours, ethanol concentrated, and water and dichloromethane were added. The organic phase was separated, dried over anhydrous sodium sulphate, and separated by thin layer chromatography to produce Compound I-3 (0.12 mmol) in a yield of 12%.

ESI(+) m/z: 559

Example 4

6-(2,6-dichloro-3,5-dimethoxyphenyl)-N-(4-(4-(2-(dimethylamino)ethyl)piperazin-1-yl)phenyl)-5,6,7,8-tetrahydropyrido[4,3-d]pyrimidin-2-amine (I-4)

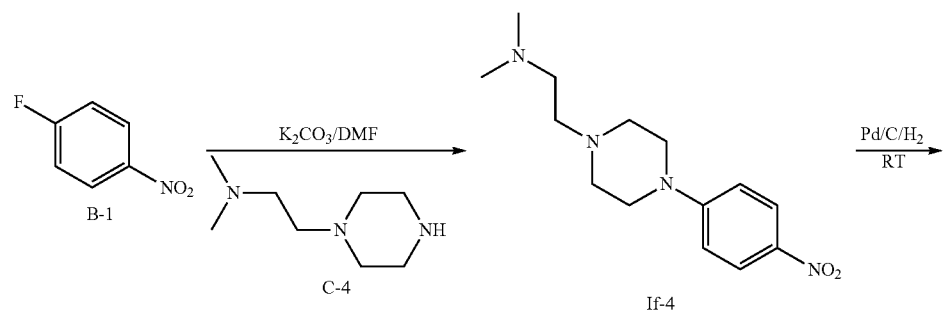

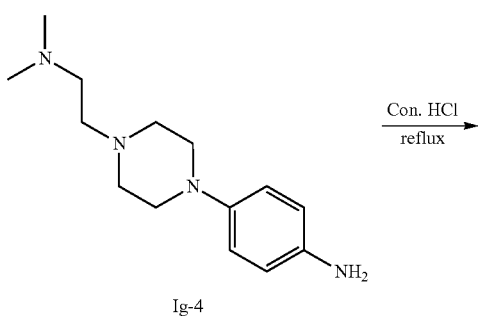

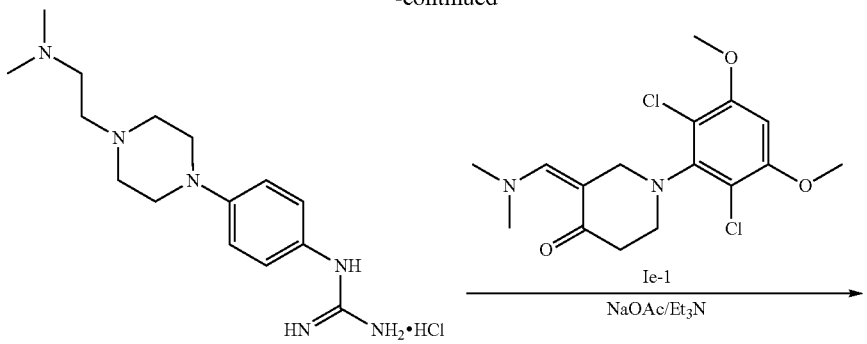

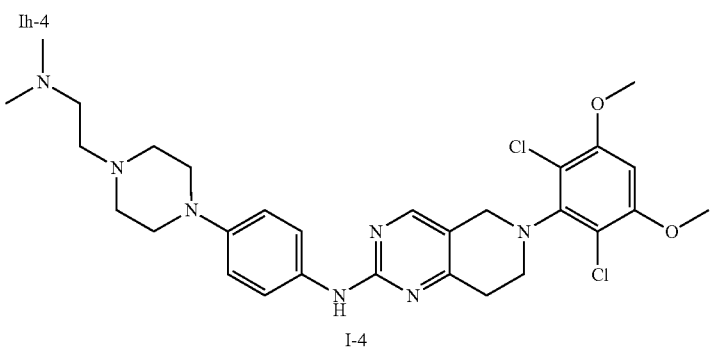

With reference to the procedure of Example 1, 2,6-dichloro-3,5-dimethoxyaniline, 4-piperidinone ethylene ketal, 1-(dimethylaminoethyl)piperazine and 1-fluoro-4-nitrobenzene were used as starting materials to synthesize and produce Compound Ih-4. Compound Ie-1 (1 mmol) and Compound Ih-4 (1.05 mmol) were dissolved in 10 ml ethanol, and sodium acetate (2 mmol) and triethylamine (1.05 mmol) were added. The mixture was stirred under flux for 7 hours, ethanol concentrated, and water and dichloromethane were added. The organic phase was separated, dried over anhydrous sodium sulphate, and separated by thin layer chromatography to produce Compound I-4 (0.09 mmol) in a yield of 9%.

ESI(+) m/z: 586

Example 5

6-(2,6-dichloro-3,5-dimethoxyphenyl)-N-(4-(4-(dimethylamino)piperidin-1-yl)phenyl)-5,6,7,8-tetrahydropyrido[4,3-d]pyrimidin-2-amine (I-5)

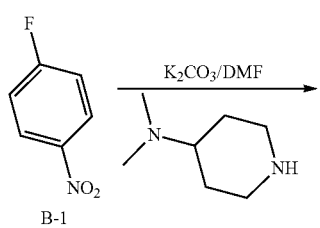

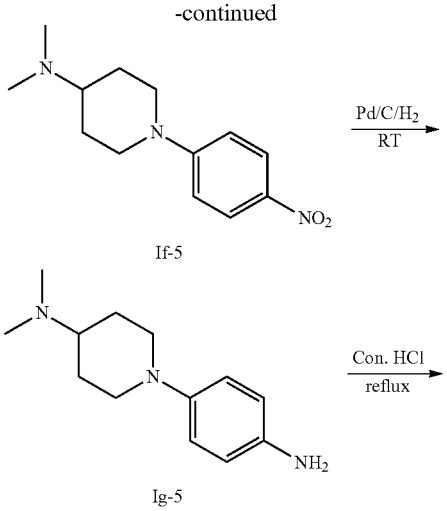

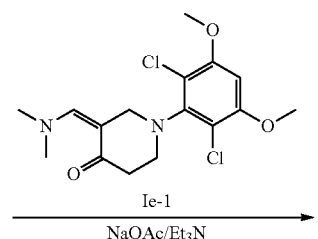

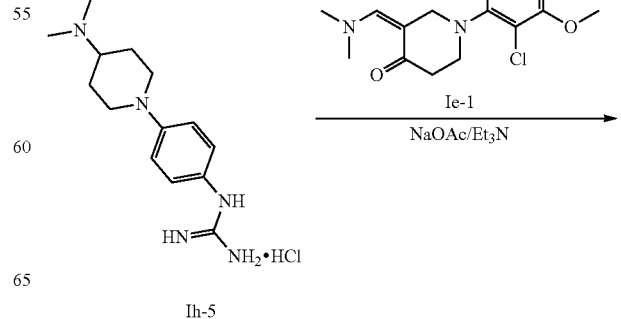

-continued

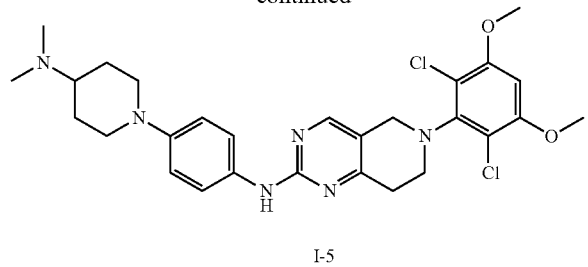

I-5

With reference to the procedure of Example 1, 2,6-dichloro-3,5-dimethoxyaniline, 4-piperidinone ethylene ketal, 4-dimethylaminopiperidine and 1-fluoro-4-nitrobenzene were used as starting materials to synthesize and produce Compound Ih-5. Compound Ie-1 (1 mmol) and Compound Ih-5 (1.05 mmol) were dissolved in 10 ml ethanol, and sodium acetate (2 mmol) and triethylamine (1.05 mmol) were added. The mixture was stirred under flux for 7 hours, ethanol concentrated, and water and dichloromethane were added. The organic phase was separated, dried over anhydrous sodium sulphate, and separated by thin layer chromatography to produce Compound I-5 (0.13 mmol) in a yield of 13%. Compound I-5 could be synthesized according to scheme II too.

ESI(+) m/z: 557

Example 6

6-(2,6-dichloro-3,5-dimethoxyphenyl)-N-(4-(4-cyclopropylpiperazin-1-yl)phenyl)-5,6,7,8-tetrahydropyrido[4,3-d]pyrimidin-2-amine (I-6)

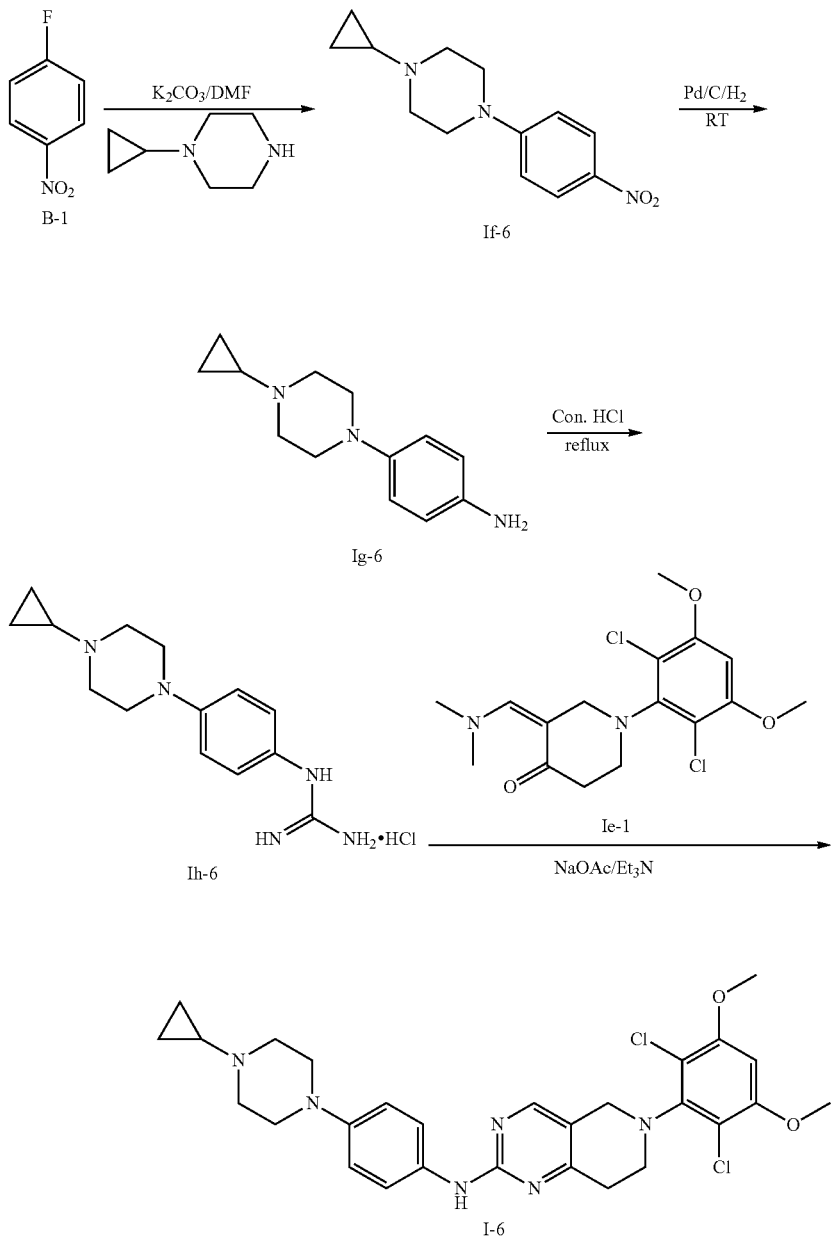

With reference to the procedure of Example 1, 2,6-dichloro-3,5-dimethoxyaniline, 4-piperidinone ethylene ketal, N-cyclopropylpiperazine and 1-fluoro-4-nitrobenzene were used as starting materials to synthesize and produce Compound Ih-6. N-cyclopropylpiperazine was synthesized according to the process described in the patent application WO2008/2816. Compound Ie-1 (1 mmol) and Compound Ih-6 (1.05 mmol) were dissolved in 10 ml ethanol, and sodium acetate (2 mmol) and triethylamine (1.05 mmol) were added. The mixture was stirred under flux for 7 hours, ethanol concentrated, and water and dichloromethane were added. The organic phase was separated, dried over anhydrous sodium sulphate, and separated by thin layer chromatography to produce Compound I-6 (0.11 mmol) in a yield of 11%.

ESI(+) m/z: 555

Example 7

1-(4-(6-(2,6-dichloro-3,5-dimethoxyphenyl)-5,6,7,8-tetrahydropyrido[4,3-d]pyrimidin-2-ylamino)phenyl-4-ethylpiperazin-2-one (I-7)

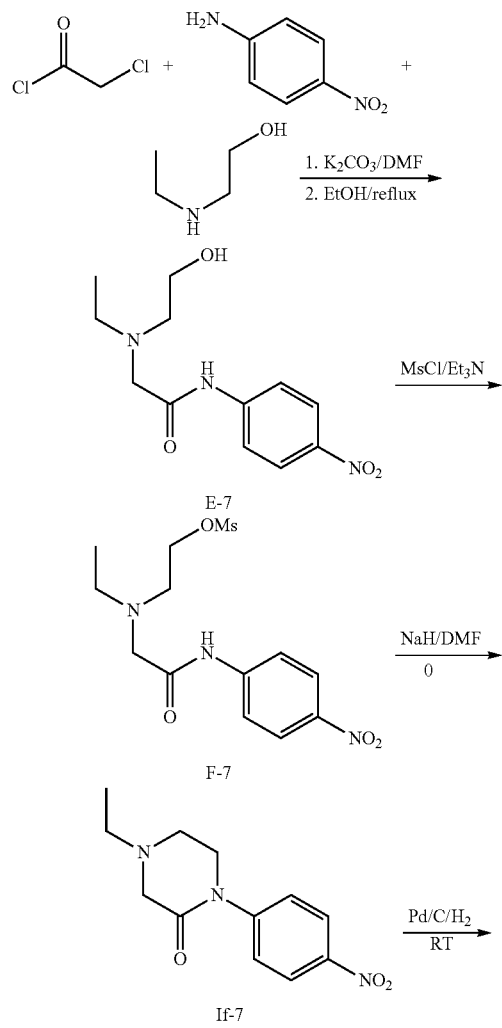

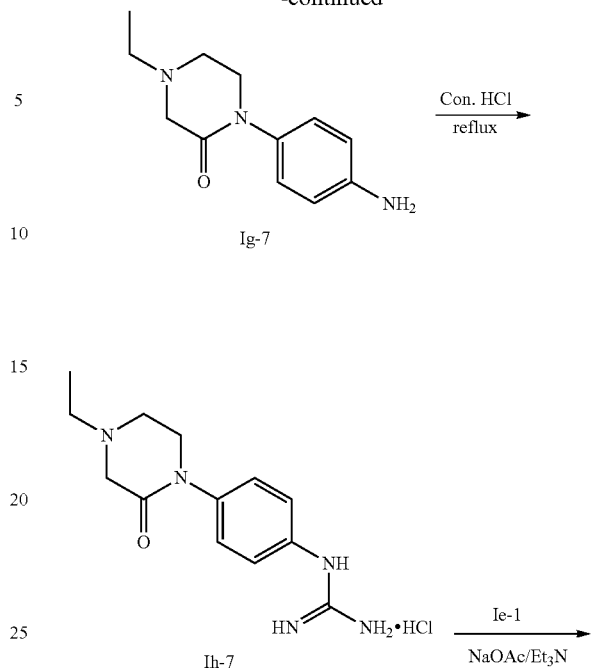

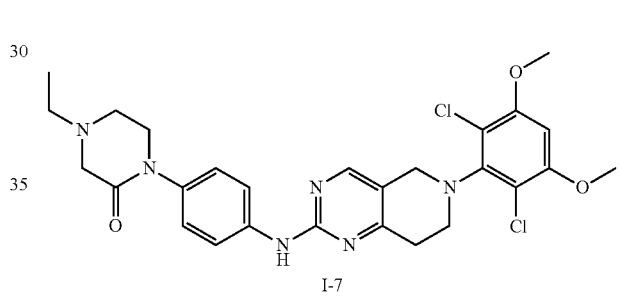

Compound E-7 was synthesized according to the scheme in the above figure. The synthesis procedure was referred to the patent application EP1775298. Compound E-7 (1.0 mmol) was dissolved in 10 ml dichloromethane, and MsCl (1.5 mmol) and triethylamine (1.1 mmol) were added in an ice bath. The mixture was stirred for 5 hours to produce Compound F-7. Compound F-7 (1.0 mmol) was dissolved in dried 3 ml DMF. The mixture was cooled to 0° C., and sodium hydride (2.5 mmol) was added. The mixture was stirred at room temperature for 6 hours to produce Compound If-7. Compound If-7 was used as the starting material, with reference to the procedure of Example 1, to synthesize and produce Compound Ih-7. Compound Ie-1 (1 mmol) and Compound Ih-7 (1.05 mmol) were dissolved in 10 ml ethanol, and sodium acetate (2 mmol) and triethylamine (1.05 mmol) were added. The mixture was stirred under flux for 7 hours, ethanol concentrated, and water and dichloromethane were added. The organic phase was separated, dried over anhydrous sodium sulphate, and separated by thin layer chromatography to produce Compound I-7 (0.14 mmol) in a yield of 14%.

ESI(+) m/z: 557

Example 8

6-(2,6-dichloro-3,5-dimethoxyphenyl)-N-(6-(4-ethylpiperazin-1-yl)pyridin-3-yl)-5,6,7,8-tetrahydropyrido[4,3-d]pyrimidin-2-amine (I-8)

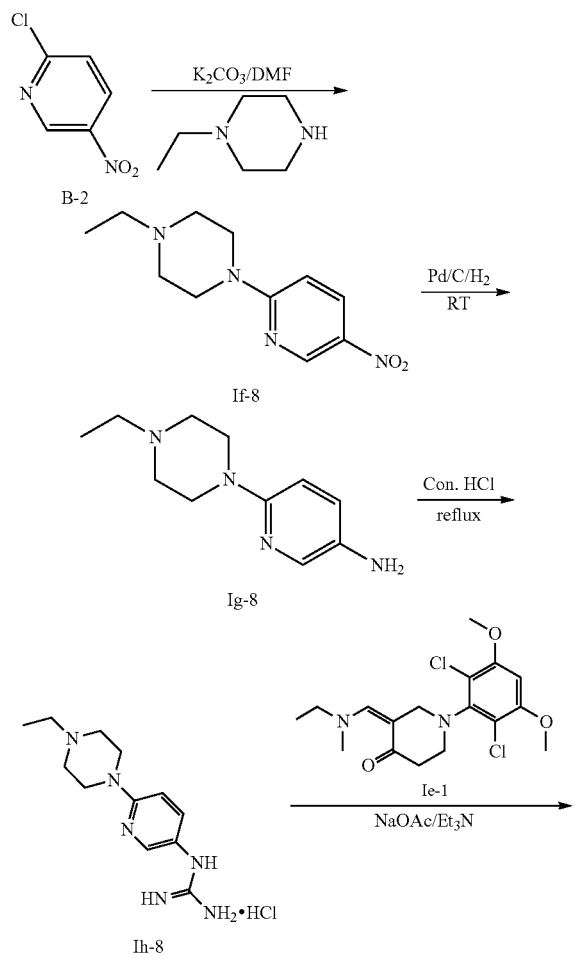

With reference to the procedure of Example 1, 2,6-dichloro-3,5-dimethoxyaniline, 4-piperidinone ethylene ketal, N-ethylpiperazine and 2-chloro-5-nitropyridine were used as starting materials to synthesize and produce Compound Ih-8. Compound Ie-1 (1 mmol) and Compound Ih-8 (1.05 mmol) were dissolved in 10 ml ethanol, and sodium acetate (2 mmol) and triethylamine (1.05 mmol) were added. The mixture was stirred under flux for 7 hours, ethanol concentrated, and water and dichloromethane were added. The organic phase was separated, dried over anhydrous sodium sulphate, and separated by thin layer chromatography to produce Compound I-8 (0.10 mmol) in a yield of 10%. Compound I-8 could be synthesized according to scheme II too.

H1-NMR (deuterated DMSO): δ9.23 (s, 1H), δ8.46 (s, 1H), δ8.19 (s, 1H), δ7.85 (d, 1H), δ6.81 (d, 2H), δ4.17 (s, 2H), δ3.91 (s, 6H), δ3.48 (t, 2H), δ3.37 (m, 4H), δ2.82 (t, 2H), δ2.46 (m, 4H), δ2.35 (m, 2H), δ1.05 (t, 3H).

ESI(+) m/z: 544

Example 9

6-(2,6-dichloro-3,5-dimethoxyphenyl)-N-(6-(4-(dimethylamino)piperidin-1-yl)pyridin-3-yl)-5,6,7,8-tetrahydropyrido[4,3-d]pyrimidin-2-amine (I-9)

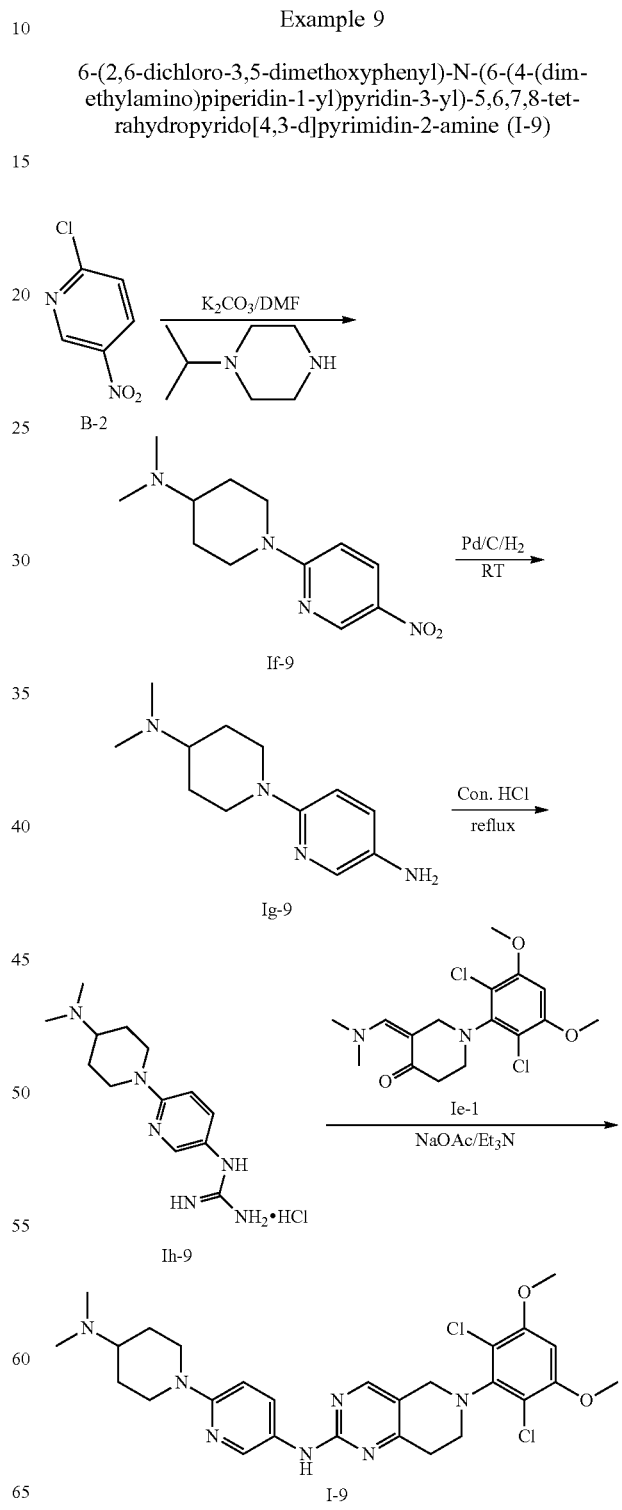

With reference to the procedure of Example 1, 2,6-dichloro-3,5-dimethoxyaniline, 4-piperidinone ethylene ketal, 4-dimethylaminopiperidine and 2-chloro-5-nitropyridine were used as starting materials to synthesize and produce Compound Ih-9. Compound Ie-1 (1 mmol) and Compound Ih-9 (1.05 mmol) were dissolved in 10 ml ethanol, and sodium acetate (2 mmol) and triethylamine (1.05 mmol) were added. The mixture was stirred under flux for 7 hours, ethanol concentrated, and water and dichloromethane were added. The organic phase was separated, dried over anhydrous sodium sulphate, and separated by thin layer chromatography to produce Compound I-9 (0.09 mmol) in a yield of 9%. Compound I-9 could be synthesized according to scheme II too.

ESI(+) m/z: 558

Example 10

6-(2,6-dichloro-3,5-dimethoxyphenyl)-N-(4-(4-ethylpiperazin-1-yl)-3-methoxyphenyl)-5,6,7,8-tetrahydropyrido[4,3-d]pyrimidin-2-amine (I-10)

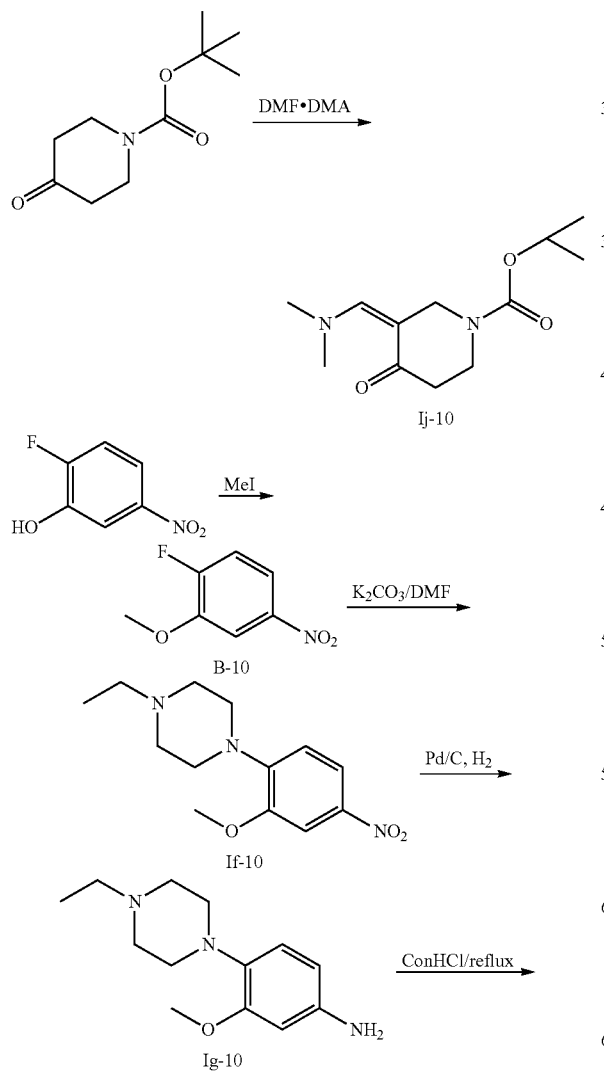

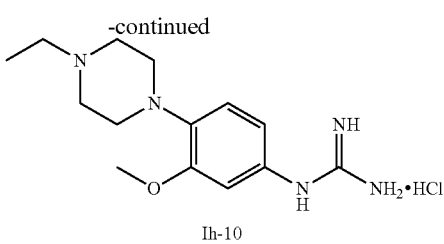

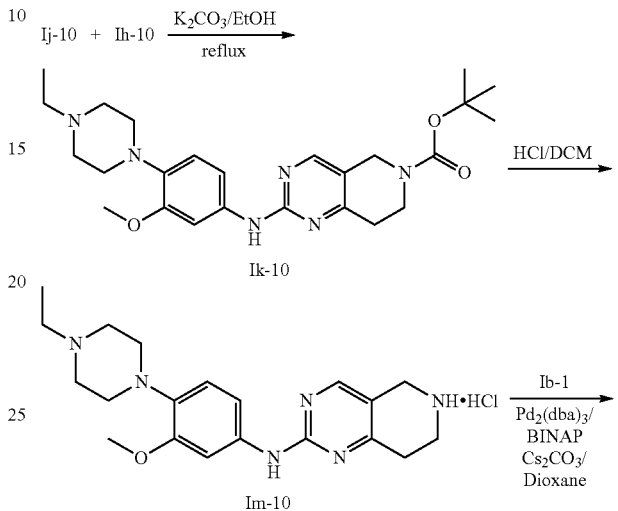

With reference to the procedure of Example 1, 2,6-dichloro-3,5-dimethoxyaniline, N-BOC-4-piperidinone, N-ethylpiperazine and 3-hydroxy-4-fluoronitrobenzene were used as starting materials to synthesize and produce Compound Ih-10.

According to scheme II, with reference to the process described in the patent application US2013/237538, Compound Ij-10 was synthesized and produced. Compound Ij-10 (1.0 mmol) and Compound Ih-10 (1.2 mmol) were dissolved in 10 ml ethanol, and potassium carbonate (1.05 mmol) was added. The mixture was stirred under flux for 2 days to produce Compound Ik-10 (0.67 mmol). Compound Ik-10 (0.25 mmol) was dissolved in 15 ml dichloromethane, and a HCl gas was introduced for 30 min. The mixture was concentrated to produce Compound Im-10 (0.25 mmol). Compound Im-10 (0.25 mmol) and Compound Ib-1 (0.26 mmol) were suspended in 10 ml dioxane, and cesium carbonate (1.1 mmol) was added. The mixture was stirred evenly, and $Pd_2(dba)_3$ (0.025 mmol) and BINAP (0.03 mmol) were added. The mixture was reacted under the nitrogen protection at 100° C. for 48 hours, cooled to room temperature, and filtered. The filtrate was concentrated to an oily substance, and an appropriate amount of methanol was added. A solid separated out. The mixture was filtered to remove the solid (BINAP), and the filtrate was separated by thin layer chromatography to produce Compound I-10 (0.028 mmol) in a yield of 11%.

ESI(+) m/z: 573

Example 11

4-chloro-3-(2-(6-(4-ethylpiperazin-1-yl)pyridin-3-ylamino)-7,8dihydropyrido[4,3-d]pyrimidin-6(5H)-yl)-5-methoxy-N-methylbenzamide (I-11)

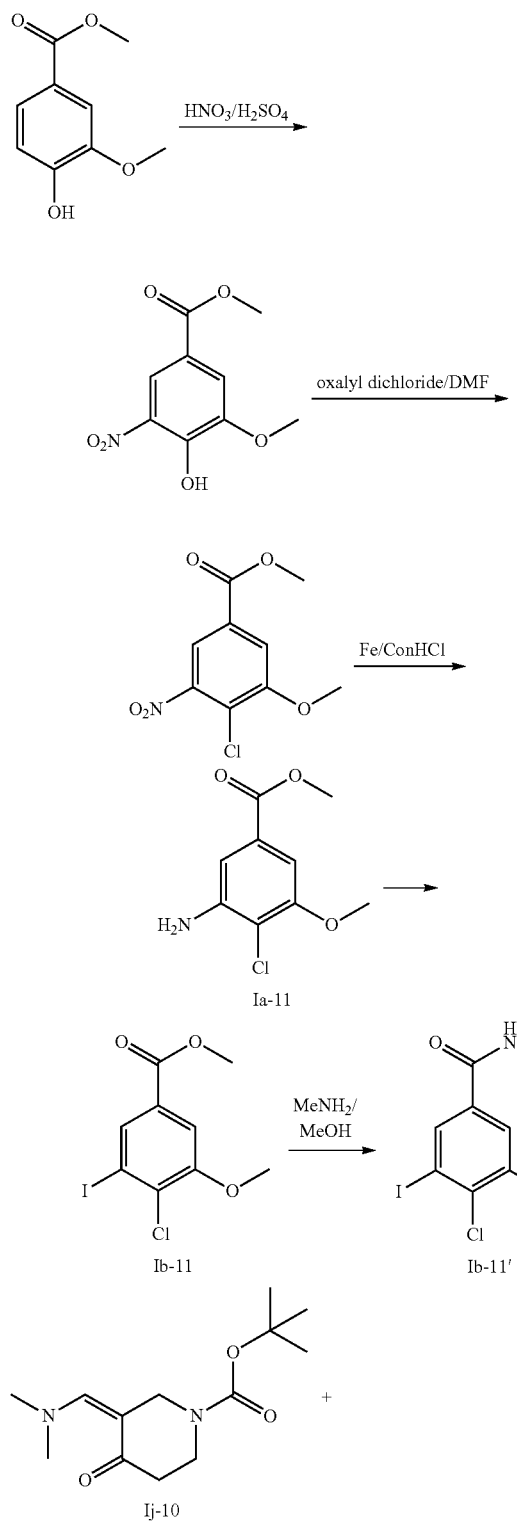

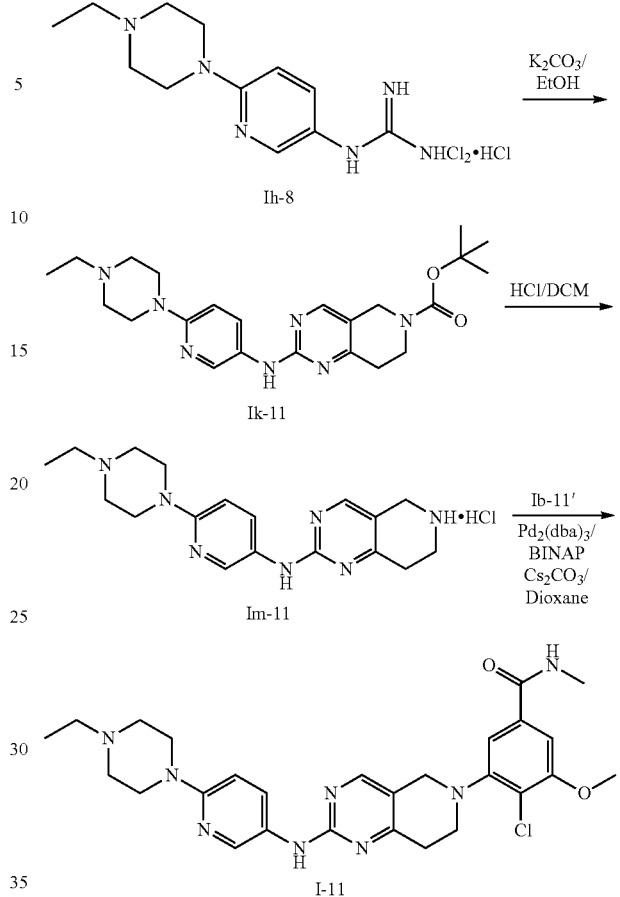

Compound Ia-11 was synthesized according to the process described in the patent application WO2011/27106. Compound Ib-11 was synthesized with reference to Example 1. In a glass sealed tube, Compound Ib-11 (9 mmol) was dissolved in 30 ml ethanol, and a methylamine alcohol solution (15 ml) was added. The mixture was reacted at 50° C. overnight to produce Compound Ib-11' (7.2 mmol).

With reference to the procedure of Example 10, methyl vanillate, N-BOC-4-piperidinone, N-ethylpiperazine and 2-chloro-5-nitropyridine were used as starting materials to synthesize and produce Compound Ik-11. Compound Ik-11 (1.0 mmol) was dissolved in 15 ml dichloromethane, and a HCl gas was introduced for 30 min. The mixture was concentrated to produce Compound Im-11 (1.0 mmol). Compound Im-11 (1.0 mmol) and Compound Ib-11' (1.05 mmol) were suspended in 10 ml dioxane, and cesium carbonate (4.5 mmol) was added. The mixture was stirred evenly, Pd$_2$(dba)$_3$ (0.1 mmol) and BINAP (0.12 mmol) were added. The mixture was reacted under the nitrogen protection at 100° C. for 48 hours, cooled to room temperature and filtered. The filtrate was concentrated to an oily substance, and an appropriate amount of methanol was added. A solid separated out. The mixture was filtered to remove the solid (BINAP), and the filtrate was separated by thin layer chromatography to produce Compound I-11 (0.2 mmol) in a yield of 20%.

H1-NMR (deuterated DMSO): δ9.3 (s, 1H), δ8.57 (s, 1H), δ8.48 (s, 1H), δ8.26 (s, 1H), δ7.89 (s, 1H), δ7.35 (d, 2H), δ6.85 (s, 1H), δ4.13 (s, 2H), δ3.91 (s, 3H), δ3.42 (m, 2H), δ3.20 (t, 4H), δ2.82 (t, 2H), δ2.68 (s, 3H), δ2.49 (m, 4H), δ2.35 (m, 2H), δ1.05 (t, 3H).

H¹-NMR (deuterated DMSO) for intermediate Ib-11': δ8.65 (s, 1H), δ7.92 (s, 1H), δ7.6 (s, 1H), δ3.91 (s, 3H), δ2.78 (d, 3H).

ESI(+) m/z: 537

Example 12

4-chloro-3-(2-(6-(4-ethylpiperazin-1-yl)pyridin-3-ylamino)-7,8dihydropyrido[4,3-d]pyrimidin-6(5H)-yl)-N,5-dimethoxybenzamide (I-12)

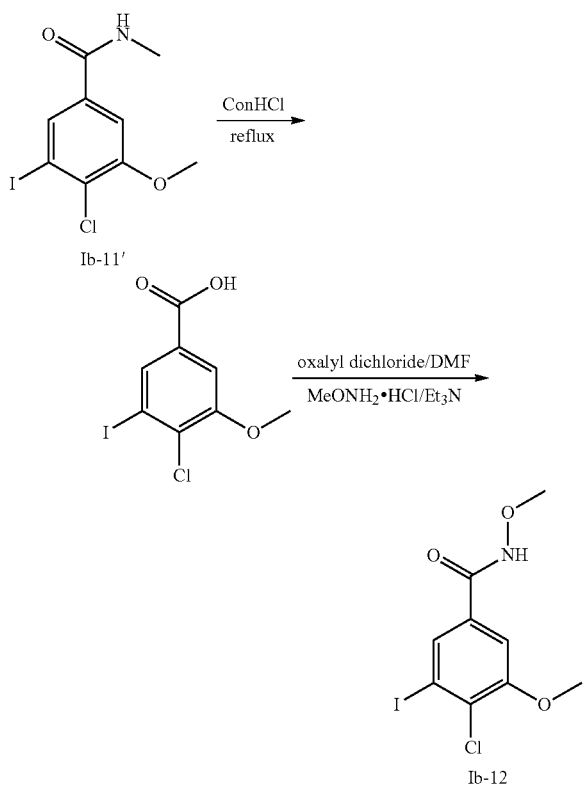

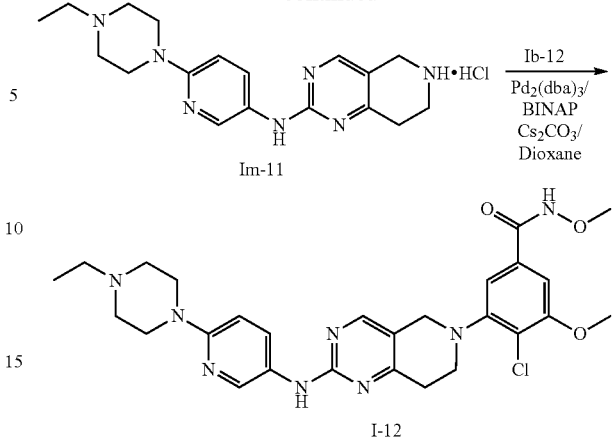

Methyl vanillate, N-BOC-4-piperidinone, N-ethylpiperazine and 2-chloro-5-nitropyridine were used as starting material, and according to the process of Example 11 to synthesize and produce Compound Im-11. Compound Ib-11' (3 mmol) was suspended in 1 ON hydrochloric acid (15 ml). The mixture was heated under reflux overnight to produce 3-iodo-4-chloro-5-methoxybenzoic acid (1.7 mmol). 3-iodo-4-chloro-5-methoxybenzoic acid (1.7 mmol) and oxalyl chloride (5.1 mmol) were reacted in presence of a catalytic amount of DMF in DCM (30 ml) in an ice bath to produce 3-iodo-4-chloro-5-methoxybenzoyl chloride. 3-iodo-4-chloro-5-methoxybenzoyl chloride was reacted with methoxyamine hydrochloride (3.4 mmol) in DCM (30 ml) and triethylamine (5.1 mmol) to produce Compound Ib-12 (0.56 mmol). Compound Im-11 (1.0 mmol) and Compound Ib-12 (1.05 mmol) were suspended in 15 ml dioxane, and cesium carbonate (4.5 mmol) was added. The mixture was stirred evenly, and Pd₂(dba)₃ (0.1 mmol) and BINAP (0.12 mmol) were added. The mixture was reacted under the nitrogen protection at 100° C. for 48 hours, cooled to room temperature and filtered. The filtrate was concentrated to an oily substance, and an appropriate amount of methanol was added. A solid separated out. The mixture was filtered to remove the solid (BINAP), and the filtrate was separated by thin layer chromatography to produce Compound I-12 (0.19 mmol) in a yield of 19%.

ESI(+) m/z: 553

Example 13

4-chloro-3-(2-(4-(4-(dimethylamino)piperazin-1-yl)phenylamino)-7,8dihydropyrido[4,3-d]pyrimidin-6(5H)-yl)-5-methoxy-N-methylbenzamide (I-13)

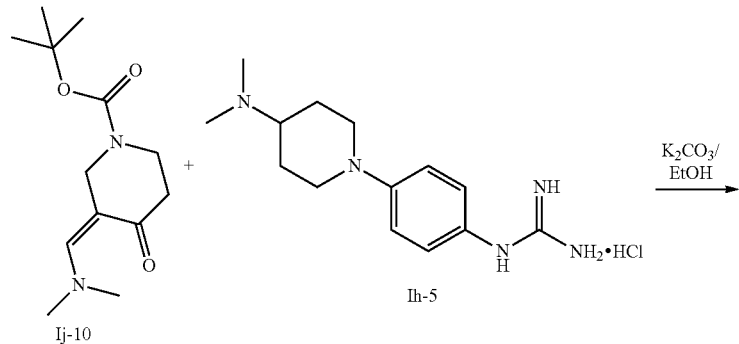

-continued

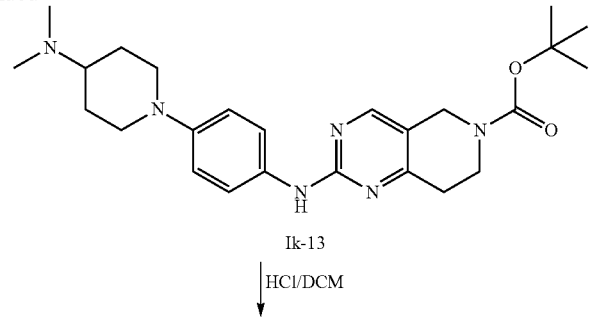

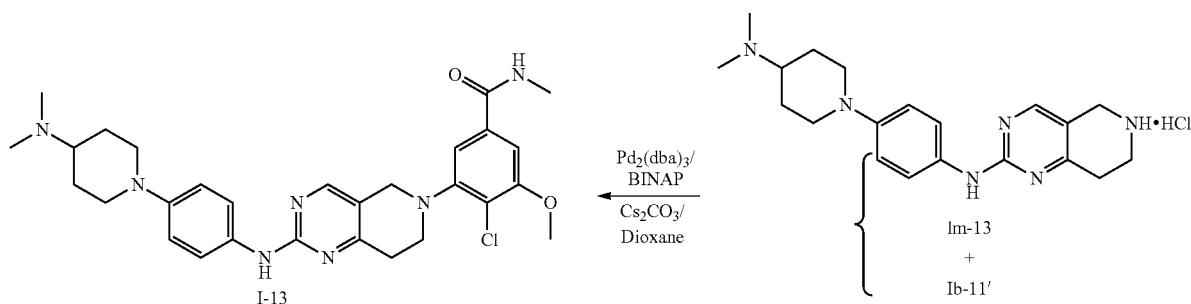

Methyl vanillate, N-BOC-4-piperidinone, 4-dimethylaminopiperidine and 1-fluoro-4-nitrobenzene were used as starting material to synthesize and produce Compound Ih-5 according to the process described in Example 5. With reference to the procedure of Example 10, Compound Ik-13 was synthesized. Compound Ik-13 (1.0 mmol) was dissolved in 15 ml dichloromethane, and a HCl gas was introduced for 30 min. The mixture was concentrated to produce Compound Im-13 (1.0 mmol). Compound Im-13 (1.0 mmol) and Compound Ib-11' (1.05 mmol) were suspended in 15 ml dioxane, and cesium carbonate (4.5 mmol) was added. The mixture was stirred evenly, and Pd$_2$(dba)$_3$ (0.1 mmol) and BINAP (0.12 mmol) were added. The mixture was reacted under the nitrogen protection at 100° C. for 48 hours, cooled to room temperature and filtered. The filtrate was concentrated to an oily substance, and an appropriate amount of methanol was added. A solid separated out. The mixture was filtered to remove the solid (BINAP), and the filtrate was separated by thin layer chromatography to produce Compound I-13 (0.14 mmol) in a yield of 14%.

ESI(+) m/z: 550

Example 14

2-(4-(5-(6-(2,6-dichloro-3,5-dimethoxyphenyl)-5,6,7,8-tetrahydropyrido[4,3-d]pyrimidin-2-ylamino)pyridin-2-yl)piperazin-1-yl)ethanol (I-14)

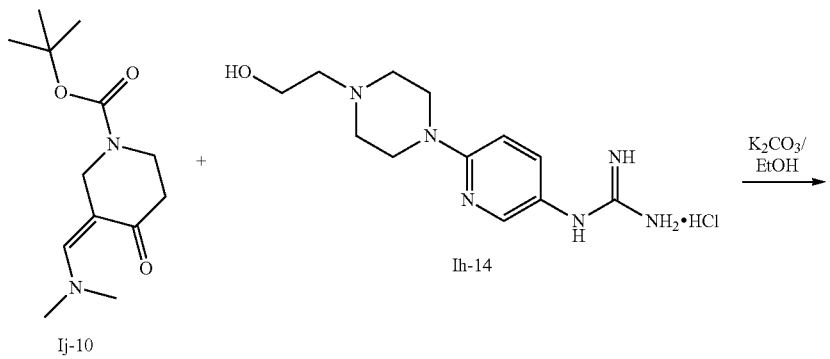

-continued

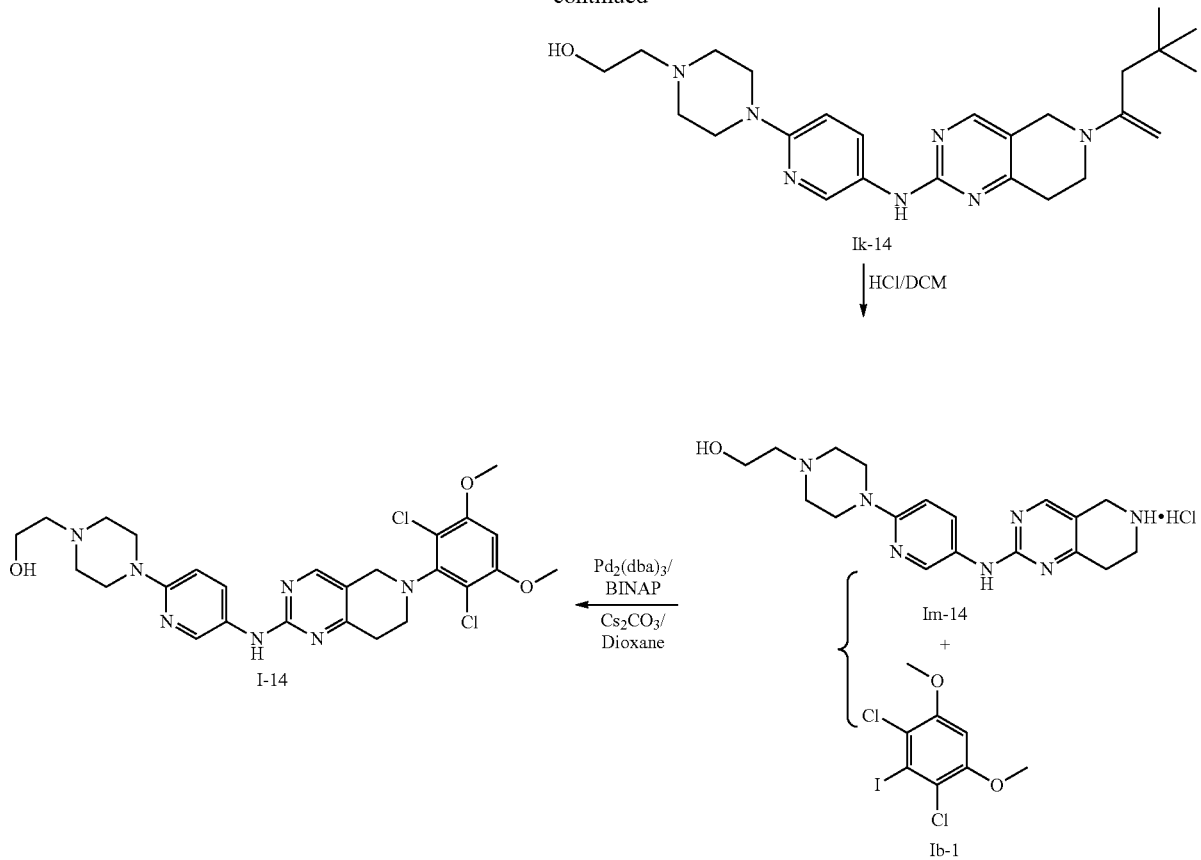

With reference to the procedure of Example 1, 2,6-dichloro-3,5-dimethoxyiodobenzene (Ib-1), N-BOC-4-piperidinone, N-hydroxyethylpiperazine and 2-chloro-5-nitropyridine were used as starting materials to synthesize and produce Compound Ih-14. With reference to the procedure of Example 10, Compound Ik-14 was synthesized and produced. Compound Ik-14 (1.0 mmol) was dissolved in 15 ml dichloromethane, and a HCl gas was introduced for 30 min. The mixture was concentrated to produce Compound Im-14 (1.0 mmol). Compound Im-14 (1.0 mmol) and 2,6-dichloro-3,5-dimethoxyiodobenzene (Ib-1, 1.05 mmol) were suspended in 10 ml dioxane, and cesium carbonate (4.5 mmol) was added. The mixture was stirred evenly, and Pd$_2$(dba)$_3$ (0.1 mmol) and BINAP (0.12 mmol) were added. The mixture was reacted under the nitrogen protection at 100° C. for 48 hours, cooled to room temperature and filtered. The filtrate was concentrated to an oily substance, and an appropriate amount of methanol was added. A solid separated out. The mixture was filtered to remove the solid (BINAP), and the filtrate was separated by thin layer chromatography to produce Compound I-14 (0.12 mmol) in a yield of 12%.

ESI(+) m/z: 560

Example 15

6-(2-fluoro-6-chloro-3,5-dimethoxyphenyl)-N-(4-(4-(dimethylamino)piperidin-1-yl)phenyl)-5,6,7,8-tetrahydropyrido[4,3-d]pyrimidin-2-amine (I-15)

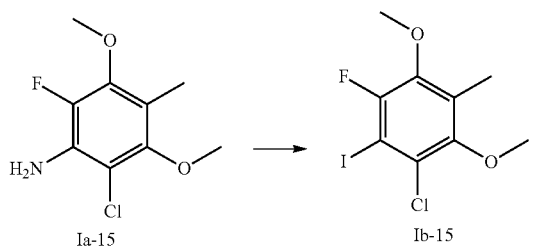

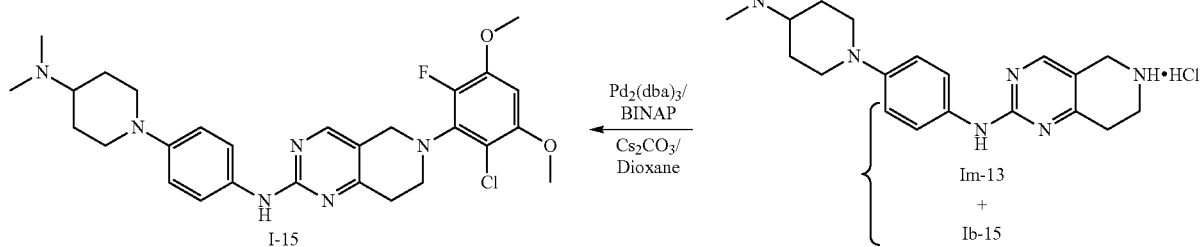

With reference to Example 63 of WO2014/7951A2, Compound Ia-15 was synthesized and produced. Then with reference to the procedure of Example 1, Compound Ib-15 was synthesized and produced from Compound Ia-15. Compound Im-13 (1.0 mmol) and Compound Ib-15 (1.05 mmol) were suspended in 15 ml dioxane, and cesium carbonate (4.5 mmol) was added. The mixture was stirred evenly, and Pd$_2$(dba)$_3$ (0.1 mmol) and BINAP (0.12 mmol) were added. The mixture was reacted under the nitrogen protection at 100° C. for 48 hours, cooled to room temperature and filtered. The filtrate was concentrated to an oily substance, and an appropriate amount of methanol was added. A solid separated out. The mixture was filtered to remove the solid (BINAP), and the filtrate was separated by thin layer chromatography to produce Compound I-15 (0.23 mmol) in a yield of 23%.

ESI(+) m/z: 541

II. Activity Test Example of the Present Compounds

Test Example 1

Proliferation Inhibition Effect on Human Acute Myelogenous Leukemia Cell KG-1α (FGFR1 Insertion Mutation), Human Gastric Cancer Cell KATO-3 (FGFR2 Amplification), Human Multiple Myeloma Cell KMS-11 (FGFR3 Y373C Mutation)

Cells in the logarithmic phase were inoculated to 96-well culture plates (cell density: 3000/well for KATO-3, 9000/well for KG-1α, 3000/well for KMS-11, cell suspension: 180 μl/well), and cultured at 37° C. under 5% CO2 for 24 hours. After the culturing, the cells adhered to the well walls. Each of compounds was dissolved in DMSO in advance to formulate a 10 mM stock solution. Upon testing, the stock solution was diluted with complete medium to 10 times the target concentration in another 96-cell plate. And then the compound was added at 20 μl/cell in the 96-well plate in which the cells were inoculated, i.e. the target concentration could be reached. The well for each concentration was triplicated, and the blank control was established. Cells continued to be cultured at 37° C. under 5% CO2 for 72 hours. After the drug acted for 72 hours, 20 μl of Thiazolyl Blue, i.e., MTT was added to each of wells. MTT was dissolved in a phosphate buffer solution free of Ca and Mg ions (D-PBSA) to formulate a 0.5% stock solution in advance. The stock solution was filtered and sterilized. Cells continued to be cultured at 37° C. under 5% CO2 for 4 hours. After 4 hours from the addition of MTT, 100 μl of 14% dimethylformamide-sodium dodecyl sulfate (DMF-SDS) was added to and dissolved in each of wells. Cells were cultured at 37° C. for 3-4 hours, and detected for the light density value (OD) at a wavelength of 570 nm. The inhibition rate was calculated based on the collected data. The result was shown in Table 1.

TABLE 1

| Compound | KG-1α (FGFR1 mutation) IC$_{50}$ (nM) | KATo-3 (FGFR2 amplification) IC$_{50}$ (nM) | KMS-11 (FGFR3 Y373C mutation) IC$_{50}$ (nM) |
|---|---|---|---|
| I-1 | 5 | 12 | / |
| I-2 | 7 | 45 | / |
| I-3 | 1 | 8 | / |
| I-4 | 2 | 30 | / |
| I-5 | 2 | 4 | / |
| I-6 | 3 | 11 | / |
| I-7 | 18 | 6 | / |
| I-8 | 5 | 4 | / |
| I-9 | 12 | 21 | 200 |
| I-10 | 24 | 7 | / |
| I-11 | 8 | 4 | / |
| I-13 | 6 | 3 | / |
| I-14 | 15 | 23 | / |
| I-15 | 2 | 3 | / |
| AZD4547 | 7 | 3 | 200 |

Note: AZD4547 was prepared with reference to Example 154 of WO 2008/75068 A2.

The test result showed: The compounds of the present invention had the proliferation inhibition effect on the human acute myelogenous leukemia cell KG-la (FGFR1 insertion mutation), the human gastric cancer cell KATO-3 (FGFR2 amplification), and the human multiple myeloma cell KMS-11 (FGFR3 Y373C mutation).

Test Example 2

Inhibition Effect on the Growth of Subcutaneously Transplanted Tumors of Human Bladder Cancer RT112/84-Bearing Nude Mice Test object: observing the inhibition effect of the drug BGJ398 and the Example Compounds of the present invention on the growth of subcutaneously transplanted tumors of human bladder cancer RT112/84-bearing nude mice and the safety of the drug BGJ398 and the Example Compounds of the present invention Test Design:

Cell cultivation: RT112/84 cells were placed in a MEM medium containing 10% fetal bovine serum (FBS) and 1% non-essential amino acid (NEAA), and cultivated in a temperature-constant incubator containing 5% CO2 at 37° C. The cells in exponential growth phase were collected and counted for inoculation.

Animal modeling and grouping: 30 BALB/c nude mice, 30 males and 0 female, 6 weeks old, 18-20 g, commercially available from Shanghai Lab. Animal Research Center. All of the test animals were maintained in a SPF facility and accommodated for the environment for at least 7 days. Cells ($5×10^6$/each mouse) were inoculated to nude mice subcutaneously at the right side of the back thereof. Each mouse was inoculated with 0.1 ml, and the tumor growth was observed regularly. After the tumors grew to 100-150 mm³ on average, the mice were divided into groups randomly according to the tumor size and the mouse weight. The grouping and the administration were shown in Table 2.

TABLE 2

| Group | n ♀ | n ♂ | Administration Group | Dosage (mg/kg) | Administration | Administration time |
|---|---|---|---|---|---|---|
| G1 | 6 | 0 | Vehicle | — | p.o. | QD × 14 |
| G2 | 6 | 0 | BGJ398 | 15 | p.o. | QD × 14 |
| G3 | 6 | 0 | Compound I-5 | 15 | p.o. | QD × 14 |
| G4 | 6 | 0 | Compound I-5 | 25 | p.o. | QD × 14 |
| G5 | 6 | 0 | Compound I-13 | 50 | p.o. | BID × 14 |

Note: Vehicle: the solvent control group; n: the animal number; the administration volume was 10 ul/g; when the animal weight was reduced by more than 15%, the administration method was correspondingly adjusted; p.o.: intragastric administration; QD×14: administration once per day, which continued for 14 days; BID×14: administration twice per day, which continued for 14 days; BGJ398 was prepared with reference to Example 145 of WO 2006/000420 A1.

Observation index: during the entire experimental process, the mouse weight and the tumor size were measured twice per week, so as to observe whether or not the toxic reaction occurs.

The tumor volume is calculated as follows:

Tumor volume (mm³)=0.5×(Tumor major diameter× Tumor minor diameter×Tumor minor diameter)

Body weight change rate (%)=measured body weight/body weight before administration× 100%.

Statistical treatment: all of the test results were expressed as average tumor volume±SE (standard error), and the significant difference between the tumor volumes of the treatment group was determined by a one-way ANOVA test, wherein $p<0.05$ represents a significant difference.

Figure 2:
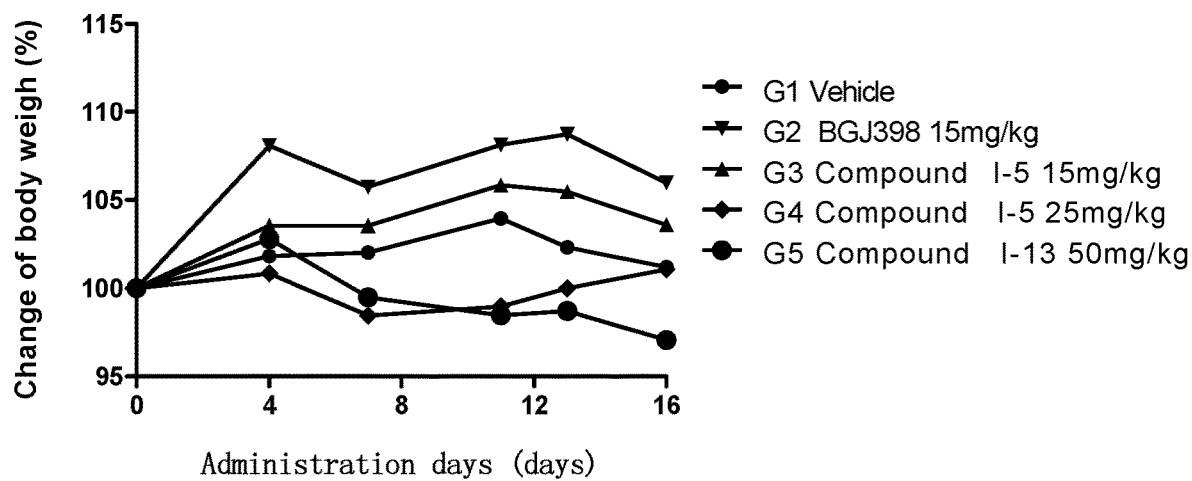
FIG. 2 is the body weight curve for human bladder cancer RT112/84-bearing nude mice for the Compounds I-5 and I-13 of the present invention and BGJ398 at their respective administration dosages.

The tumor growth curves of five experimental groups are shown in FIG. 1, and the mice's weight growth curves are shown in FIG. 2. The results show that the compounds of the present invention have a good inhibition effect on the growth of subcutaneously transplanted tumors of human bladder cancer RT112/84-bearing nude mice (for the same dosage, Compound I-5 of the present invention had a better inhibition effect than BGJ398), while having little effect on the weights of nude mice, and showing a good safety.

All of the literatures mentioned herein are incorporated into the present application by reference. It should be also noted that, upon reading the above-mentioned contents of the present application, a person skilled in the art can modify, change or amend the present invention without departing from the spirits of the present invention, and these equivalents are also within the scope as defined by the claims appended in the present application.

The invention claimed is:

1. A compound represented by general formula (I), or a pharmaceutically acceptable salt thereof,

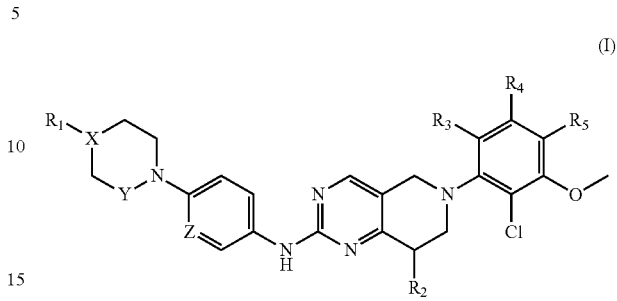

(I)

wherein:

X is $CR_6$ or N;

Y is $CR_6R_7$ or $C(=O)$;

Z is $CR_6$ or N;

$R_1$ is selected from the group consisting of H, halogen, hydroxy, —$C_1$-$C_6$alkyl, —$C_1$-$C_6$alkoxy, —$C_1$-$C_6$alkylthio, —$C_3$-$C_6$cycloalkyl, halo$C_1$-$C_6$alkyl, hydroxy$C_1$-$C_6$alkyl, —$(CH_2)_n$—$NR_6R_7$ and $C_3$-$C_6$cycloalkyl or 4-7 membered heterocycloalkyl, which can be optionally substituted with one or more groups selected from the group consisting of halogen, hydroxy, —$C_1$-$C_6$alkyl, —$C_1$-$C_6$alkoxy, —$C_1$-$C_6$alkylthio, and —$NH_2$;

$R_2$ is selected from the group consisting of H, halogen, hydroxy, —$C_1$-$C_6$alkyl, —$C_1$-$C_6$alkoxy or —$C_3$-$C_6$cycloalkyl;

$R_3$, $R_4$ and $R_5$ are each independently selected from the group consisting of H, halogen, hydroxy, —$C_1$-$C_6$alkyl, —$C_1$-$C_6$alkoxy, —$C_3$-$C_6$cycloalkyl, —O—$C_3$-$C_6$cycloalkyl, —$C_1$-$C_6$alkylthio, halo$C_1$-$C_6$alkyl, hydroxy$C_1$-$C_6$alkyl, —$C(=O)$—$NR_6R_7$, —$NR_6R_7$, —$OC(=O)R_6$, —$COOR_6$, —$NR_6C(=O)R_7$, —$NR_6COOR_7$ and —$OSO_2R_6$;

$R_6$ and $R_7$ are each independently selected from the group consisting of H, —$C_1$-$C_6$alkyl, —$C_1$-$C_6$alkoxy, —$C_3$-$C_6$cycloalkyl or —$C_1$-$C_6$alkylthio;

n is 0, 1, 2, 3 or 4.

2. The compound according to claim 1 or a pharmaceutically acceptable salt thereof, wherein said compound is a compound represented by formula (II), a compound represented by formula (III), a compound represented by formula (IV) or a compound represented by formula (V), wherein each of substituent variables has the same meaning as those in claim 1,

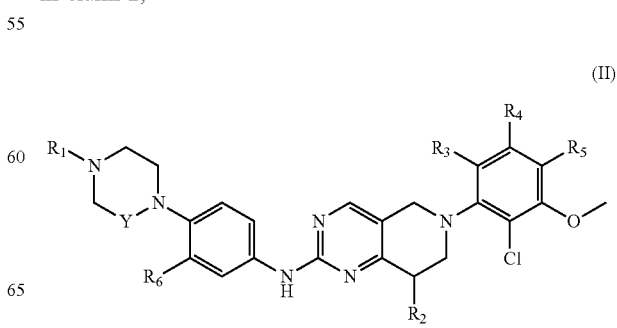

(II)

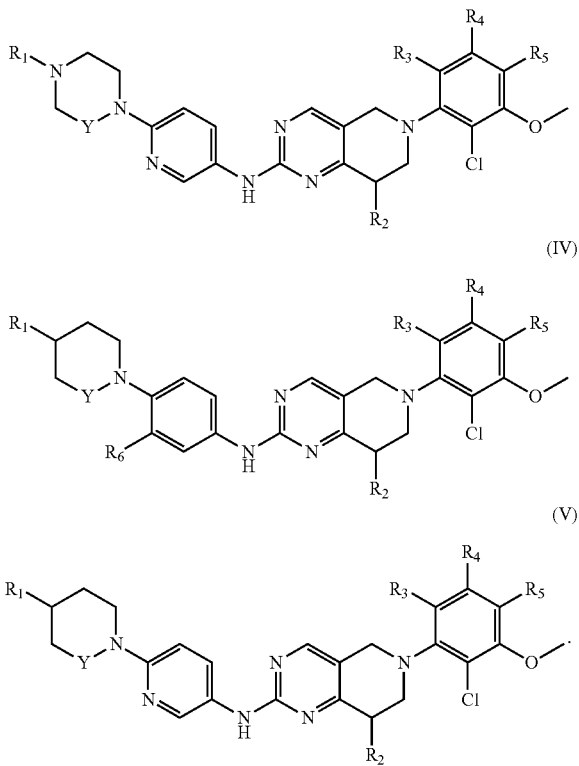

3. The compound according to claim 2 or a pharmaceutically acceptable salt thereof, wherein for the compound represented by formula (II) and the compound represented by formula (IV), the substituent $R_6$ of the benzene ring is selected from the group consisting of H, —$C_1$-$C_6$alkyl or —$C_1$-$C_6$alkoxy.

4. The compound according to claim 1 or a pharmaceutically acceptable salt thereof, wherein Y is $CR_6R_7$, wherein $R_6$ and $R_7$ are each independently selected from the group consisting of H or —$C_1$-$C_6$alkyl.

5. The compound according to claim 1 or a pharmaceutically acceptable salt thereof, wherein $R_1$ is selected from the group consisting of H, halogen, hydroxy, —$C_1$-$C_6$alkyl, —$C_1$-$C_6$alkoxy, —$C_1$-$C_6$alkylthio, —$C_3$-$C_6$cycloalkyl, halo$C_1$-$C_6$alkyl, hydroxy$C_1$-$C_6$alkyl, and —$(CH_2)_n$—$NR_6R_7$, wherein $R_6$ and $R_7$ are each independently selected from the group consisting of H, —$C_1$-$C_6$alkyl or —$C_1$-$C_6$alkoxy, n is 0, 1, 2 or 3.

6. The compound according to claim 5 or a pharmaceutically acceptable salt thereof, wherein $R_1$ is selected from the group consisting of H, hydroxy, —$C_1$-$C_6$alkyl, —$C_1$-$C_6$alkoxy, —$C_3$-$C_6$cycloalkyl, halo$C_1$-$C_6$alkyl, hydroxy$C_1$-$C_6$alkyl, —$(CH_2)_n$—$NR_6R_7$, wherein $R_6$ and $R_7$ are each independently selected from the group consisting of H, —$C_1$-$C_6$alkyl or —$C_1$-$C_6$alkoxy, n is 0, 1 or 2.

7. The compound according to claim 6 or a pharmaceutically acceptable salt thereof, wherein $R_1$ is selected from the group consisting of H, hydroxy, —$C_1$-$C_4$alkyl, —$C_1$-$C_4$alkoxy, —$C_3$-$C_6$cycloalkyl, halo$C_1$-$C_4$alkyl, hydroxy$C_1$-$C_4$alkyl, —$(CH_2)_n$—$NR_6R_7$, wherein $R_6$ and $R_7$ are each independently selected from the group consisting of H, —$C_1$-$C_4$alkyl or —$C_1$-$C_4$alkoxy, n is 0, 1 or 2.

8. The compound according to claim 1 or a pharmaceutically acceptable salt thereof, wherein $R_2$ is selected from the group consisting of H, halogen, hydroxy or —$C_1$-$C_4$alkyl.

9. The compound according to claim 1 or a pharmaceutically acceptable salt thereof, wherein $R_3$, $R_4$ and $R_5$ are each independently selected from the group consisting of H, halogen, hydroxy, —$C_1$-$C_6$alkyl, —$C_1$-$C_6$alkoxy, —$C_3$-$C_6$cycloalkyl, —O—$C_3$-$C_6$cycloalkyl, —$C_1$-$C_6$alkylthio, halo$C_1$-$C_6$alkyl, hydroxy$C_1$-$C_6$alkyl, and —C(=O)—$NR_6R_7$, and $R_3$, $R_4$ and $R_5$ are not H at the same time, wherein $R_6$ and $R_7$ are each independently selected from the group consisting of H, —$C_1$-$C_6$alkyl or —$C_1$-$C_6$alkoxy.

10. The compound according to claim 9 or a pharmaceutically acceptable salt thereof, wherein $R_3$, $R_4$ and $R_5$ are each independently selected from the group consisting of H, halogen, hydroxy, —$C_1$-$C_6$alkyl, —$C_1$-$C_6$alkoxy, —C(=O)—$NR_6R_7$, and $R_3$, $R_4$ and $R_5$ are not H at the same time, wherein $R_6$ and $R_7$ are each independently selected from the group consisting of H, —$C_1$-$C_6$alkyl or —$C_1$-$C_6$alkoxy.

11. The compound according to claim 10 or a pharmaceutically acceptable salt thereof, wherein $R_3$, $R_4$ and $R_5$ are each independently selected from the group consisting of H, halogen, hydroxy, —$C_1$-$C_4$alkyl, —$C_1$-$C_4$alkoxy, and —C(=O)—$NR_6R_7$, and $R_3$, $R_4$ and $R_5$ are not H at the same time, wherein $R_6$ and $R_7$ are each independently selected from the group consisting of H, —$C_1$-$C_4$alkyl or —$C_1$-$C_4$alkoxy.

12. The compound according to claim 1 or a pharmaceutically acceptable salt thereof, wherein said compound is selected from the group consisting of:
  6-(2,6-dichloro-3,5-dimethoxyphenyl)-N-(4-(4-ethylpiperazin-1-yl)phenyl)-5,6,7,8-tetrahydropyrido[4,3-d]pyrimidin-2-amine;
  6-(2,6-dichloro-3,5-dimethoxyphenyl)-N-(4-(4-(2,2,2-trifluoroethyl)piperazin-1-yl)phenyl)-5,6,7,8-tetrahydropyrido[4,3-d]pyrimidin-2-amine;
  2-(4-(4-(6-(2,6-dichloro-3,5-dimethoxyphenyl)-5,6,7,8-tetrahydropyrido[4,3-d]pyrimidin-2-ylamino)phenyl)piperazin-1-yl)ethanol;
  6-(2,6-dichloro-3,5-dimethoxyphenyl)-N-(4-(4-(2-(dimethylamino)ethyl)piperazin-1-yl)phenyl)-5,6,7,8-tetrahydropyrido[4,3-d]pyrimidin-2-amine;
  6-(2,6-dichloro-3,5-dimethoxyphenyl)-N-(4-(4-(dimethylamino)piperidin-1-yl)phenyl)-5,6,7,8-tetrahydropyrido[4,3-d]pyrimidin-2-amine;
  6-(2,6-dichloro-3,5-dimethoxyphenyl)-N-(4-(4-cyclopropylpiperazin-1-yl)phenyl)-5,6,7,8-tetrahydropyrido[4,3-d]pyrimidin-2-amine;
  1-(4-(6-(2,6-dichloro-3,5-dimethoxyphenyl)-5,6,7,8-tetrahydropyrido[4,3-d]pyrimidin-2-ylamino)phenyl-4-ethylpiperazin-2-one;
  6-(2,6-dichloro-3,5-dimethoxyphenyl)-N-(6-(4-ethylpiperazin-1-yl)pyridin-3-yl)-5,6,7,8-tetrahydropyrido[4,3-d]pyrimidin-2-amine;
  6-(2,6-dichloro-3,5-dimethoxyphenyl)-N-(6-(4-(dimethylamino)piperidin-1-yl)pyridin-3-yl)-5,6,7,8-tetrahydropyrido[4,3-d]pyrimidin-2-amine;
  6-(2,6-dichloro-3,5-dimethoxyphenyl)-N-(4-(4-ethylpiperazin-1-yl)-3-methoxyphenyl)-5,6,7,8-tetrahydropyrido[4,3-d]pyrimidin-2-amine;
  4-chloro-3-(2-(6-(4-ethylpiperazin-1-yl)pyridin-3-ylamino)-7,8dihydropyrido[4,3-d]pyrimidin-6(5H)-yl)-5-methoxy-N-methylbenzamide;
  4-chloro-3-(2-(6-(4-ethylpiperazin-1-yl)pyridin-3-ylamino)-7,8dihydropyrido[4,3-d]pyrimidin-6(5H)-yl)-N,5-dimethoxybenzamide;
  4-chloro-3-(2-(4-(4-(dimethylamino)piperazin-1-yl)phenylamino)-7,8dihydropyrido[4,3-d]pyrimidin-6(5H)-yl)-5-methoxy-N-methylbenzamide;

2-(4-(5-(6-(2,6-dichloro-3,5-dimethoxyphenyl)-5,6,7,8-tetrahydropyrido[4,3-d]pyrimidin-2-ylamino)pyridin-2-yl)piperazin-1-yl)ethanol;

6-(2-fluoro-6-chloro-3,5-dimethoxyphenyl)-N-(4-(4-(dimethylamino)piperidin-1-yl)phenyl)-5,6,7,8-tetrahydropyrido[4,3-d]pyrimidin-2-amine.

13. A process for preparing the compound represented by formula (I) according to claim 1, which comprises the steps of:

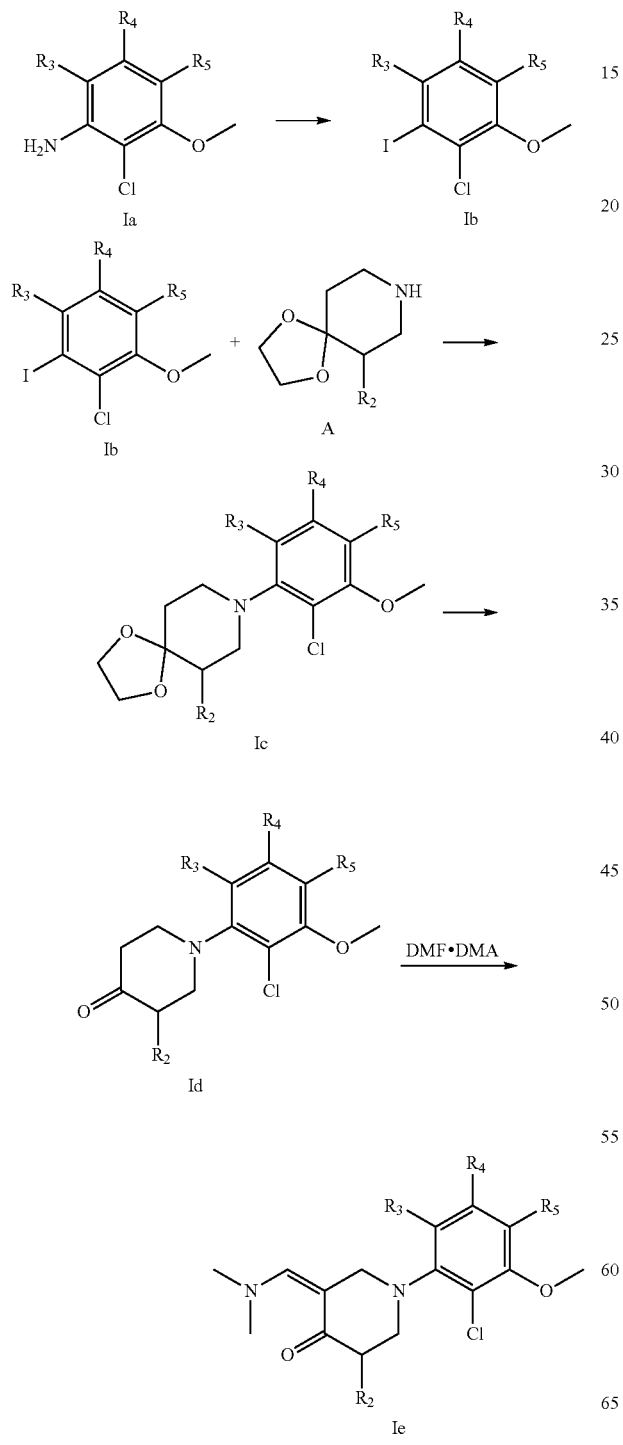

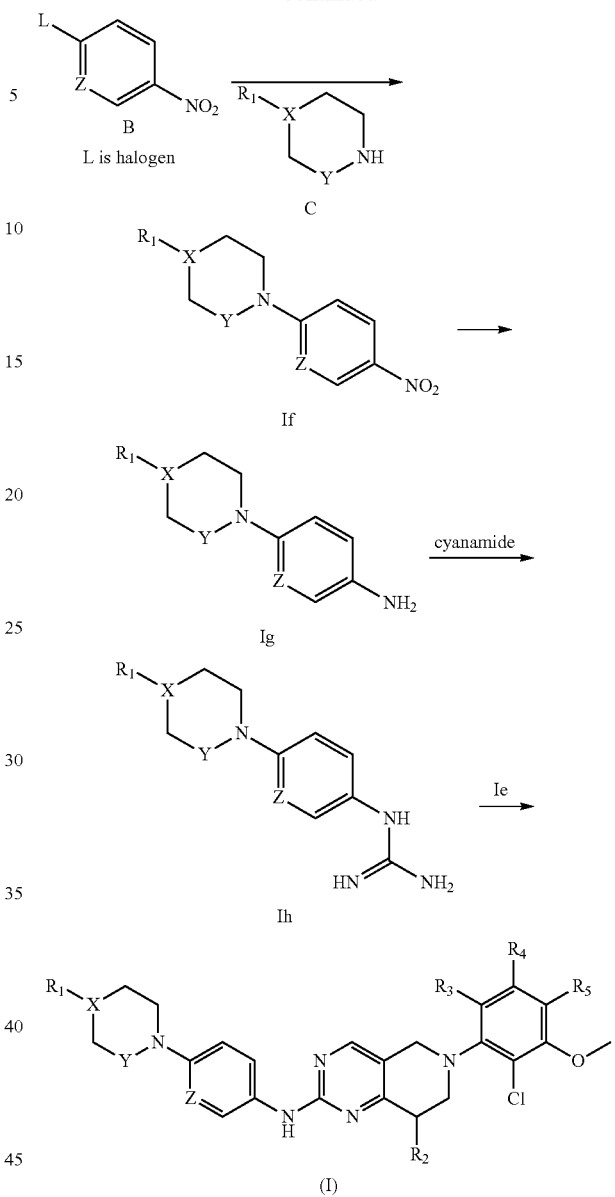

wherein $R_1$, $R_2$, $R_3$, $R_4$, $R_5$, X, Y and Z are defined as those in claim 1;

Compound Ia is used as starting material and reacted by diazotization to produce Compound Ib; Compound Ib and starting material A are reacted by coupling in a basic condition to produce Compound Ic; Compound Ic is hydrolyzed to produce Compound Id; Compound Id and DMF.DMA are reacted by formylation to produce Compound Ie;

starting materials B and C are reacted by substitution in a basic condition to produce Compound If; Compound If is catalytically hydrogenated to produce Compound Ig; Compound Ig and cyanoamine are reacted by nucleophilic addition to produce Compound Ih; Compound Ih and Compound Ie are finally reacted by ring closing in a basic condition to produce the compound represented by formula (I).

14. A process for preparing the compound represented by formula (I) according to claim 1, which comprises the steps of:

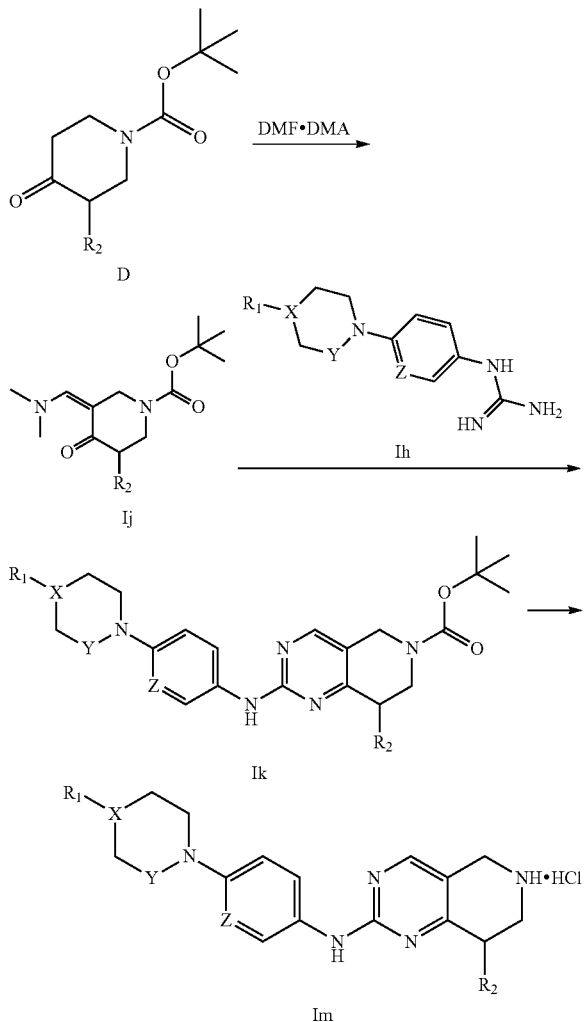

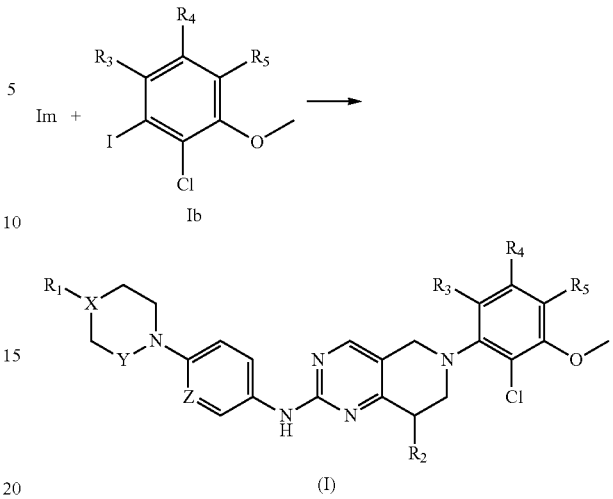

wherein $R_1$, $R_2$, $R_3$, $R_a$, $R_5$, X, Y and Z are defined as those in claim 1;

Starting compound D and DMF.DMA are reacted by formylation to produce Compound Ij; Compound Ij and Compound Ih are reacted by ring closing in a basic condition to produce Compound Ik; Compound Ik is deprotected in an acidic condition to form a salt and produce Compound Im; Compound Im and Compound Ib are finally reacted by coupling in a basic condition to produce the compound represented by formula (I).

15. A pharmaceutical composition, comprising the compound according to claim 1 or a pharmaceutically acceptable salt thereof and a pharmaceutically acceptable carrier.

16. A method of treating FGFR kinase mediated bladder cancer comprising administering the compound according to claim 1 or a pharmaceutically acceptable salt thereof.

17. A method of treating bladder cancer comprising administering the compound according to claim 1 or a pharmaceutically acceptable salt thereof.

* * * * *